US009696279B2

(12) United States Patent
Hartwig et al.

(10) Patent No.: US 9,696,279 B2
(45) Date of Patent: Jul. 4, 2017

(54) DETECTION SYSTEM FOR DETECTING MAGNETIC OBJECTS IN THE HUMAN ORGANISM

(75) Inventors: Benedikt Hartwig, Darmstadt (DE); Peter Niepoth, Gross-Umstadt (DE); Steffen Junginger, Rostock (DE); Hans-Joachim Stiller, Rostock (DE); Norbert Windhab, Hofheim (DE); Gerhard Geipel, Haltern am See (DE)

(73) Assignee: Evonik Roehm GmbH, Darmstadt (DE)

( * ) Notice: Subject to any disclaimer, the term of this patent is extended or adjusted under 35 U.S.C. 154(b) by 149 days.

(21) Appl. No.: 14/367,682

(22) PCT Filed: Jan. 9, 2012

(86) PCT No.: PCT/EP2012/050217
§ 371 (c)(1),
(2), (4) Date: Jul. 2, 2014

(87) PCT Pub. No.: WO2013/091901
PCT Pub. Date: Jun. 27, 2013

(65) Prior Publication Data
US 2015/0008914 A1    Jan. 8, 2015

(30) Foreign Application Priority Data

Dec. 21, 2011 (DE) .................... 10 2011 089 334

(51) Int. Cl.
*A61B 5/05* (2006.01)
*G01N 27/72* (2006.01)
(Continued)

(52) U.S. Cl.
CPC .............. *G01N 27/72* (2013.01); *A61B 1/041* (2013.01); *A61B 5/0515* (2013.01); *A61B 5/062* (2013.01);
(Continued)

(58) Field of Classification Search
CPC ...... G01N 27/72; A61B 5/0515; A61B 5/073; A61B 1/041; A61B 5/062; G01R 33/10; G01R 33/028; G01R 33/096
(Continued)

(56) References Cited

U.S. PATENT DOCUMENTS 6,082,366 A * 7/2000 Andra ................. A61B 5/06
128/899
2001/0026222 A1* 10/2001 Canady, Jr. ............ A61B 5/113
340/573.1
(Continued)

FOREIGN PATENT DOCUMENTS

CN          1195404 A      10/1998
DE       39 40 260 A1       9/1990
(Continued)

OTHER PUBLICATIONS

Chao Hu, et al., "A Cubic 3-Axis Magnetic Sensor Array for Wirelessly Tracking Magnet Position and Orientation", IEEE Sensor Journal, vol. 10, No. 5, pp. 903-913, (May 1, 2010) XP011306917.
(Continued)

*Primary Examiner* — Sanjay Cattungal
(74) *Attorney, Agent, or Firm* — Oblon, McClelland, Maier & Neustadt, L.L.P.

(57) ABSTRACT

The subject matter of the invention is a detector system for detecting magnetic bodies in the human organism, which comprises at least two sensor assemblies, wherein each sensor assembly has one, two or three anisotropic magnetic resistance sensors, of which the axes of weak magnetization point in different directions in pairs, and each sensor assembly has a spacing of 0.5 to 50 cm from the sensor assembly or the other sensor assemblies, and at least two sensor assemblies are tilted at an angle of 0 to 45° with respect to one another, and in addition a method for detecting the
(Continued)

Figure 1A:
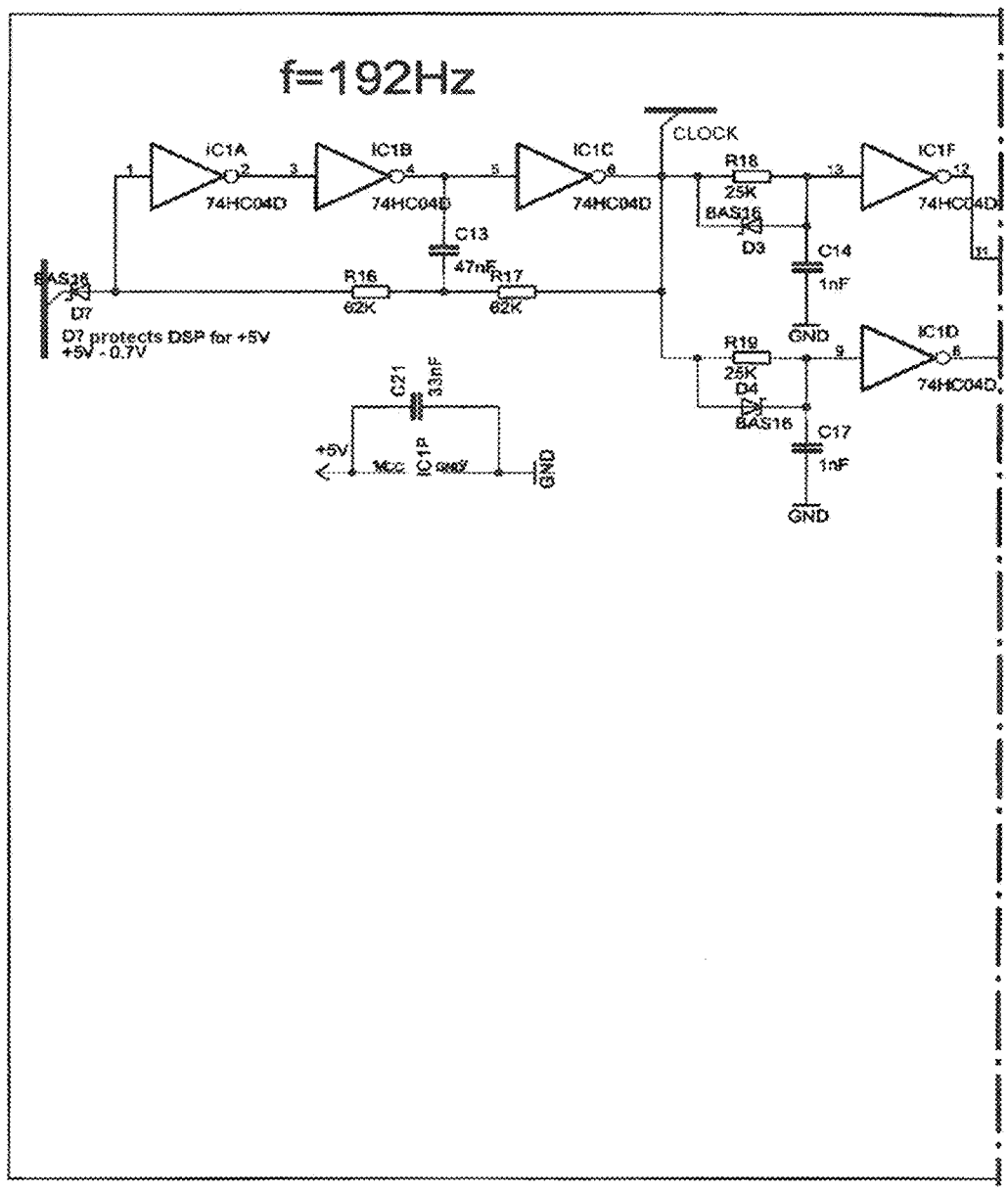

magnetic flux produced by a magnetic body in the human organism, and the use of the detector system according to the invention for detecting swallowed magnetic bodies and the disintegration of the same in the digestive system.

13 Claims, 22 Drawing Sheets

(51) Int. Cl.
    *A61B 1/04*     (2006.01)
    *A61B 5/06*     (2006.01)
    *G01R 33/09*     (2006.01)
    *G01R 33/028*     (2006.01)
    *G01R 33/10*     (2006.01)
    *A61B 5/07*     (2006.01)

(52) U.S. Cl.
    CPC ............ *A61B 5/073* (2013.01); *G01R 33/028* (2013.01); *G01R 33/096* (2013.01); *G01R 33/10* (2013.01)

(58) Field of Classification Search
    USPC ........................... 600/407–430; 324/318–322
    See application file for complete search history.

(56) References Cited

U.S. PATENT DOCUMENTS

2007/0167743 A1* 7/2007 Honda ................... A61B 1/041
                                                                                    600/424

2011/0244599 A1* 10/2011 Whig ..................... B82Y 25/00
                                                                                     438/3

FOREIGN PATENT DOCUMENTS

| JP | 7-294400 A | 11/1995 |
| JP | 11-512007 A | 10/1999 |
| JP | 2005-502868 A | 1/2005 |
| WO | 97 09640 | 3/1997 |
| WO | WO 2011/026808 A1 | 3/2011 |

OTHER PUBLICATIONS

International Search Report Issued Oct. 24, 2012 in PCT/EP12/050217 Filed Jan. 9, 2012.
Michael Hocke, et al., "Every slow-wave impulse is associated with motor activity of the human stomach", American Physiological Society, vol. 296, Dec. 8, 2008, pp. 709-716.
Office Action issued Sep. 28, 2015 in Japanese Patent Application No. 2014-547770 (with English language translation).
Combined Office Action and Search Report issued Oct. 23, 2015 in Chinese Patent Application No. 201280070051.0 (with English language translation).
Office Action issued Nov. 27, 2015 in Mexican Patent Application No. MX/a/2014/007081 (with English language translation).
Office Action issued May 10, 2016 in Russian Patent Application No. 2014129629.

\* cited by examiner

DETECTION SYSTEM FOR DETECTING MAGNETIC OBJECTS IN THE HUMAN ORGANISM

The invention relates to the technical implementation of a sensor assembly which is able to detect magnetic or magnetized oral administration forms after the oral ingestion thereof and follows the dissolution of the same via the reduction or disappearance of the magnetic field from the oral administration form.

Techniques for measuring magnetic fluxes have been known for a long time. There are sensors which can measure the magnetic flux density vector with high sensitivity in a relatively small space, for example sensors based on the functional principle of the anisotropic magnetoresistive effect, abbreviated AMR effect. In the AMR effect, in specific materials the ohmic resistance depends on the angle between the current flow and the magnetization vector. It can be observed particularly well in thin layers of Permalloy, an alloy of 81% Ni and 19% Fe. In commercial sensors, four individual resistors are wired up into a Wheatstone bridge. By using the so-called barber pole structure, an angle of 45° is imposed between the magnetization vector and the current flowing through the respective resistor. In the absence of an external magnetic field, the magnetization vector is oriented along the longitudinal axis of the resistor, the so-called axis of weak magnetization. If an external magnetic field is applied, the magnetization vector is rotated though an angle with respect to this axis. As a result, the angle between the current flow and the magnetization vector changes, which is in turn associated with a change in the non-reactive resistance.

Patent application WO 2011/026808 A1 discloses a computer-based evaluation system which detects the magnetic flux from an oral administration form which is equipped with magnetized phases. The various phases of the administration form can be designed such that, following oral ingestion, they dissolve at different times in the human digestive system. The evaluation system measures the magnetic field resulting from the superimposition of the magnetic phases discontinuously with the aid of a Hall sensor, which is fixed to a Petri dish. Assuming that magnetic fields in the human body are detected at a distance of 5-20 cm to the surface of the skin, the system uses the resultant magnetic field to generate a signature, by detecting which the time of incorporation and the dissolution, but also the characteristic design of the administration form, are identified. However, no information is given as to how such a signal can be obtained if the person moves together with the evaluation system, nor as to how an evaluable signal can be detected if interfering magnetic fields which do not originate from the administration form are measured at the same time.

In the article bearing the title "*Every slow-wave impulse is associated with motor activity of the human stomach*", from Dec. 8, 2008 at the American Physiological Society, Michael Hocke, Ulrike Schöne et al. describe a system which detects the movements of small magnetic markers in the human stomach. While the patient must lie quietly, the stationary system, which comprises 9 magnetic field sensors, is brought into position. As soon as neither interfering magnetic fields are present nor so-called "artifacts", which cannot be assigned unambiguously to the marker, the measurements can be carried out.

The object of the present invention was therefore, with the aid of a system, to detect small changes in the magnetic field which, during daily life, are brought about by an administered magnetic body. A further object consisted in providing a method for obtaining a measured signal and the evaluation of the latter, with which an administered magnetic body in the human organism is detected in daily life.

Within the context of the invention, the interfering magnetic field from the surroundings is assumed to be homogenous but not constant over time. This is because the sensor assembly and the magnetic bodies can move in the surrounding magnetic field. In addition, the magnetic body is moved relative to the sensor assembly (swallowing, positional changes in the stomach) and changes its magnetic properties as a result of disintegration with a predefined time dependence. Furthermore, numerous objects which change the magnetic field of the surroundings occur, for example vehicles, metallic furniture, lines through which power flows and the like. The magnetic flux density of the surrounding field, for example the Earth's magnetic field, is around 35 $\mu T$. Within the context of the invention, the measurement of magnetic flux densities with the aid of a Tesla meter at at least 1 cm distance is assumed.

Magnetic bodies, for example magnetite pressed into cylinders with the dimensions of a few millimeters, produce magnetic fluxes of a few 100 nT in the length scales of a few centimeters to 0.5 m of interest within the context of the invention. The compensation of interfering fluxes or the detection of the same in the measured signal is also critical for the usability of the detector system.

Surprisingly, the object is achieved by means of a detector system comprising at least two sensor assemblies, wherein each sensor assembly has one, two or three anisotropic magnetic resistance sensors. The axes of the weak magnetization of the magnetic resistance sensors point in different directions in pairs, and each sensor assembly has a spacing of 0.5 to 50 cm from the sensor assembly or the other sensor assemblies. At least two sensor assemblies are tilted at an angle of 0 to 45° with respect to one another.

The subject matter of the invention is therefore a detector system for detecting magnetic bodies in the human organism which has at least two sensor assemblies, wherein each sensor assembly has one, two or three anisotropic magnetic resistance sensors, of which the axes of weak magnetization point in different directions in pairs, and each sensor assembly has a spacing of 0.5 to 50 cm from the sensor assembly or the other sensor assemblies, and at least two sensor assemblies are tilted at an angle of 0 to 45° with respect to one another.

The term "anisotropic magnetic resistance sensor" is abbreviated to "AMR sensor" in the context of the invention.

The invention will be explained in more detail below.

The sensor assembly can be integrated into a strap, into the clothing, into jewelry or decorative articles, into an armband, for example in a wristwatch, or fixed directly to the body or carried by means of a suction cup or fastening aid. Preferably, the detector system according to the invention can be carried along on the body by means of a strap, since the strap, into which the sensor assemblies can be integrated, is provided to be worn on the person and is fitted to the person without or with the help of a third party. This strap can be, for example, a belt, which restricts its wearer only minimally in his everyday movements. The strap can advantageously be a combined breast and shoulder strap. Particularly advantageously, the combined breast and shoulder strap can be a strap system which is known from the sport of climbing. The combined breast and shoulder strap has the advantage of not restricting the person during his everyday movements when worn, and of positioning the sensor assemblies with high accuracy relative to the esophagus and the alimentary tract. The strap system additionally has the particular advantage of keeping the sensor assemblies of the detector system according to the invention particularly accurately respectively at a defined distance and the axes of weak magnetization thereof at a defined angle. The strap permits its wearer full mobility during everyday tasks, in particular during actions at work and leisure. The detector system according to the invention can also be carried along on any article which is carried along in the vicinity of the body or on the body of the person, for example a wheelchair, walker, a cradle, couch, or fitted to crutches, or in a wristwatch, in an armband, chain or decorative article.

If a sensor assembly of the detector system according to the invention has only one AMR sensor, this is also called "single-channel" in the context of the invention; in the case of 3 AMR sensors, accordingly "three-channel". If a sensor assembly has, for example, 3 AMR sensors, the easily magnetizable axes of which are arranged like the coordinate axes x, y and z of a Cartesian coordinate system, then the components of the vector of said sensor assembly are the measured signals in the x, y and in the z direction, the signals $S_x$, $S_y$ and $S_z$. They are the measure of the magnetic flux density in the direction of the coordinate axes.

The axes of weak magnetization of a sensor assembly meet at an imaginary point, the origin of the respective sensor assembly. The distance between these origins or, in the case of three sensor assemblies, the pairwise distance between these origins, within the context of the invention is the distance or the pairwise distance between the sensor assemblies.

The axes of weak magnetization of the second sensor assembly each lie parallel to the coordinate axes x, y and z or at an angle thereto. Within the context of the invention, this angle is defined as follows: the axes of weak magnetization of each sensor assembly each lie on an imaginary conical shell of a spatial angle. Within the context of the invention, the angle at which the two sensor assemblies of the detector system according to the invention are tilted with respect to each other is the angle between the central axes of the cone of the sensor assemblies.

If the detector system is carried along in a strap, armband or object in the vicinity of the body, within the context of the accuracy with which the strap can be adjusted, the angle lies in the plane which is defined by the origins of the sensor assemblies and the point of entry of the esophagus into the stomach. Particularly high accuracies are achieved if this object is a strap system known from the sport of climbing.

If the detector system according to the invention has two sensor assemblies, the directions and the signals are numbered consecutively. Accordingly, in the directions x1, y1, z1 and x2, y2, z2, respectively, the signals $S_{x1}$, $S_{y1}$, and $S_{z1}$ and $S_{x2}$, $S_{y2}$, and $S_{z2}$, are obtained, from which the vectors $S_1$ and $S_2$ are formed:

$$S_1 = (S_{x1}, S_{y1}, S_{z1}), \text{ and}$$

$$S_2 = (S_{x2}, S_{y2}, S_{z2}).$$

If, for example, the first of the sensor assemblies of the detector system according to the invention is only one AMR sensor, namely in the direction x1, the vector $S_1$ is simplified to $$S_1 = (S_{x1}, 0, 0).$$

The detector system according to the invention has the advantage of measuring these vector components so accurately in each case and making them evaluable in such a way that, during the movement of the sensor assembly by the wearer, the fluctuation in the magnitude of these vectors remains small or is known to such an extent that the change in the measured values caused by a magnetic body is detected. Thus, the influence of external interfering sources is detected and eliminated or can be filtered out of the measured signal.

The magnitude of the vectors, abbreviated to $|S_1|$ and $|S_2|$, is calculated in a known way:

$$|S_1| = (S_{x1}^2 + S_{y1}^2 + S_{z1}^2)^{1/2},$$

$$|S_2| (S_{x2}^2 + S_{y2}^2 + S_{z2}^2)^{1/2}.$$

If there is a short distance between the sensor assemblies, equal measured values result in homogenous fields. A magnetic body having low magnetic induction in the vicinity of the sensors, as a result of the magnetic field thereof decaying quickly with the distance from the sensor, influences the measured values thereof at different distances from the sensors. However, since each sensor assembly supplies a vector which is composed of the measured signals from the AMR sensors, the detector system according to the invention has the advantage that the proximity of the magnetic body to the sensor assemblies has an effect on the angle between the measured vectors. If the magnetic body moves, this angle changes.

The measuring sensitivity can be increased by advantageous embodiments of the detector system according to the invention.

Preferably, at least one, preferably each AMR sensor of the detector system has 4 barber pole elements, which are connected together to form a Wheatstone bridge or a Wheatstone bridge equivalent circuit. The axis of weak magnetization is then the resultant of the axes of weak magnetization of the individual barber pole elements. External magnetic fields detune such a Wheatstone bridge much more intensely than, for example a resistance bridge having only one barber pole element and three conventional non-reactive resistors. Accordingly, the sensitivity of a Wheatstone bridge made of 4 barber pole elements is increased.

In specialist circles, it is known that the characteristic curve of the AMR Sensor can be changed by intense magnetic fields, since domains of the anisotropic material are reformed or deformed, or because the walls thereof in the material are displaced. This effect can be counteracted by at least one set and/or reset pulse, which is output once before the measurement, preferably multiple times during the measurement, particularly preferably periodically during the measurement, via a set-reset strap. The action of periodically output set and/or reset pulses consists in ensuring the optimal characteristic curve of the AMR sensors.

Alternating the set and reset pulse, called "flipping" within the context of the invention, permits the elimination of offset errors by means of forming the difference between the signals measured after each pulse. Furthermore, thermal, electrical and/or influences which, for example, occur during the heating of the AMR sensor, are eliminated.

Likewise, by using the flipping, automatic adjustment of the working point of the following amplifier is made possible, which, within the scope of the invention, is called "switching feedback". In addition to the mark/space ratio, reliable achievement of the saturation induction by the set and reset pulses is also important.

Figure 1B:
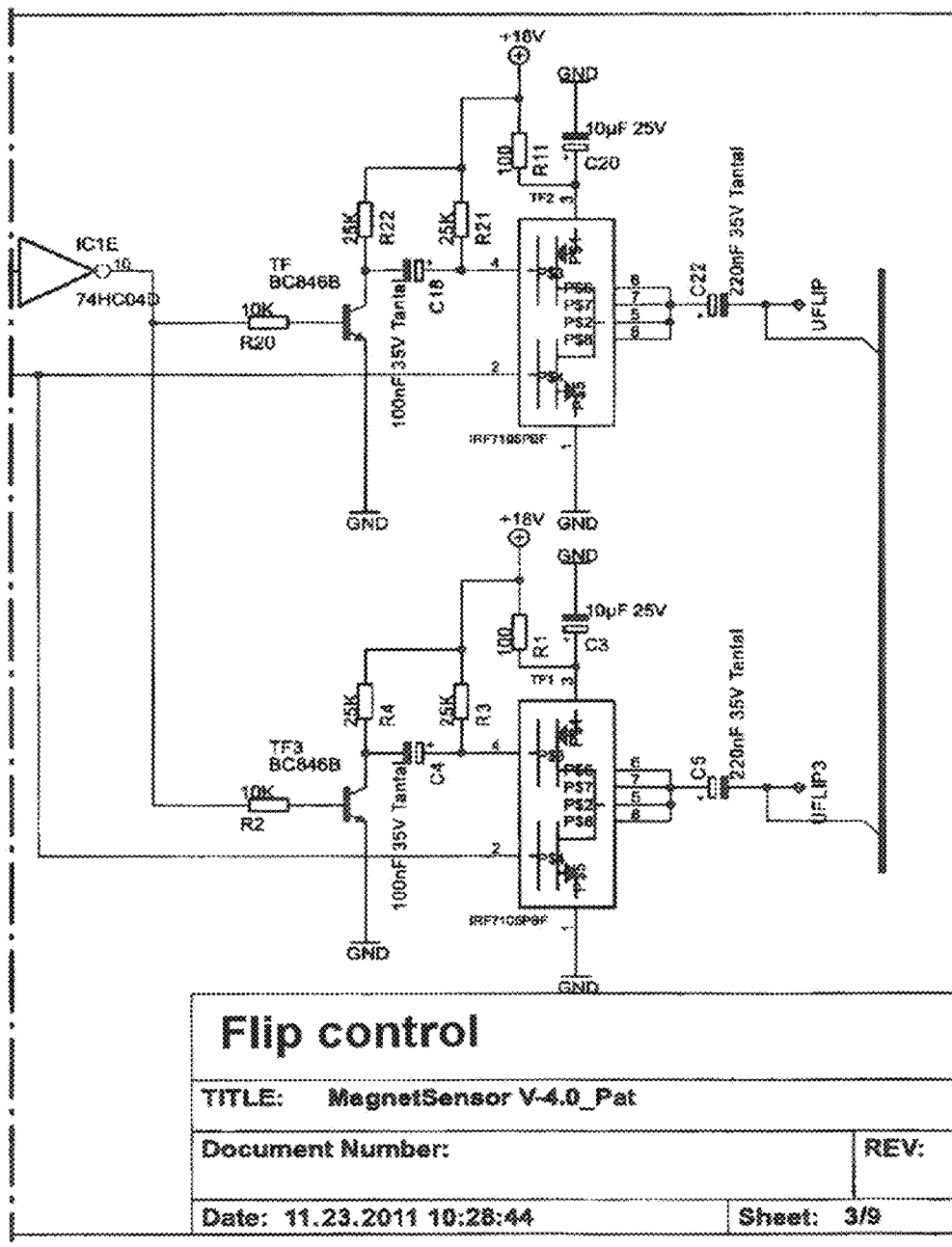

FIGS. 1A and 1B show the circuit diagram according to which flipping is made possible. When forming the difference, the working point for the following amplifier must be adjusted. Inaccuracies in this adjustment in the case of a very large control range have an effect as a result of an asymmetrically established limitation of the signal.

In addition, the detector system according to the invention can have an offset strap. The current through the offset strap can be supplied by a driver circuit which, example, can contain an amplifier in a bridge circuit as an important element. The offset strap permits the compensation of the field component to be measured by generating a field having an opposed orientation. Without an offset strap, during the measurement of the magnetic flux density, the nonlinearity of the sensor characteristic curve and, in addition, the cross-sensitivity of the AMR sensors has to be taken into account. The cross-sensitivity consists in the action of high values of the magnetic flux density in both one axial direction and also on the measured value from an AMR sensor oriented orthogonally thereto.

With an offset strap, however, the bridge voltage of the sensor in a control loop is minimized by feeding a current into the offset strap. The current required for the bridge compensation in the offset strap is a measure of the field to be measured. As a result, measurements are always made at the same working point of the sensor characteristic curve at which the sensitivity and linearity have their maximum and, at the same time, the cross-sensitivity vanishes. The detector system according to the invention is therefore suitable for any everyday environment.

Figure 2A:
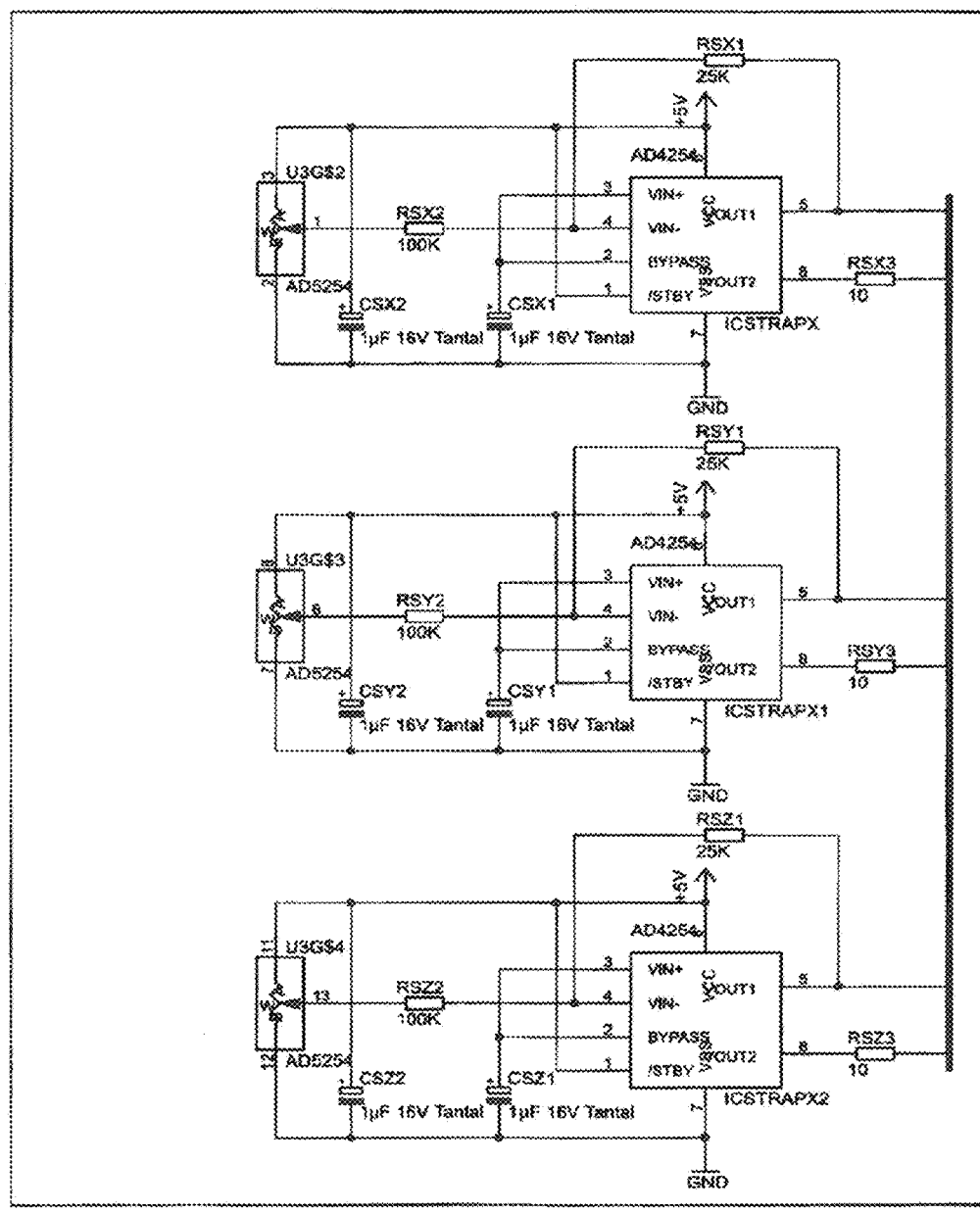
Figure 2B:
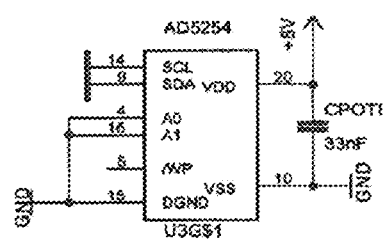

The offset strap is connected to the "offset strap driver". The circuit diagram is shown by FIGS. 2A and 2B.

In general, nonlinearities and cross-sensitivities can be detected during the calibration and the measured result can be corrected appropriately. As a result, operation without activating the offset strap is also possible, with minimized energy consumption.

There is a further alternative to the compensation of the field component to be measured by generating a field with opposite orientation by means of feeding a current into the offset strap. In this case, at least one, preferably every AMR Sensor of the detector system according to the invention, can be equipped with an alternative circuit.

In this embodiment of the detector system, the bridge voltage from the sensor is not controlled out to the set point zero in a negative feedback circuit. Instead, by means of a DA converter and an amplifier, a defined current is fed into the offset strap in such a way that there is no departure from a specific control range of the sensor bridge.

In a further possible way of implementing the detector system according to the invention, the control range of the sensor characteristic curve can be subdivided into a number of segments, for example into 256 segments in the case of a DA converter having 8 bit resolution. In order to ensure a continuous measurement with a changing magnetic field strength, the segments can be chosen in such a way that there is a sufficient overlap of adjacent segments. Each of these segments can then be provided with only a small control range around the optimal working point of the AMR sensor. The reduction in the control range reduces the cross-sensitivity and the effects of nonlinearities of the characteristic curve. Complete correction of nonlinearity and cross-sensitivity is dispensed with. For this purpose, however, improved amplitude resolution of the measurement is obtained by means of the combination of AD converter and segmentation of the characteristic curve.

For this purpose, for each of the segments of an AMR sensor measuring range, the parameters of the approximation by a straight line in each case, together with their associated slope and height section, must be determined. The slopes and height sections of the segments are provided via the calibration data of the sensors. If the detector system according to the invention is moved only during daily use, for example by the daily movements of its wearer, then the defined current and therefore the approximation are continuously tracked.

Depending on the speed at which the movements are made, a high scanning rate is advantageous, so that a continuous measurement is implemented without any overloads.

The advantage of this variant consists in the fact that, given appropriately fast scanning, the offset straps have to be operated with only a very small mark/space ratio. As a result, the power demand and the inherent heating of the sensors and offset problems associated therewith are reduced sharply.

In addition, by using fast AD and DA converters at the measuring frequency necessary for the continuous measurement in the magnetic field, the time needed for the individual measurement can be kept low. It is therefore possible to activate the offset straps only during the time necessary to acquire the measured value. If the activation of the offset straps is carried out, for example, only with a mark/space ratio of 0.1, for example with a 1 ms measuring period and a time interval of 10 ms between successive measurements, then the power loss is reduced. As a result, less heat is developed and thus the drift of the measured signals is reduced or even suppressed.

For the usability of the detector system according to the invention having two sensor assemblies, care must be taken that the esophagus has a length of 20 to 30 cm and is passed through in 5 to 10 seconds by a swallowed object. This results in a speed range during the esophagus passage of 2 to 6 cm/s and therefore a correspondingly rapidly changing signal for the detector system. The frequency range of the useful signal therefore coincides with the frequency range possessed by some of the external interference signals. Within the context of the invention, "external interference signals" denotes those signals which are caused by magnetic fluxes which surround the wearer and in which he—necessarily—moves, for example in the Earth's magnetic field or in the surroundings of magnetic objects such as, for example, vehicles. Because of external interference signals, no ability to distinguish between a passage of a magnetic object through the esophagus and magnetic fluxes from other objects would be expected. In particular, filtering of the measured signal in accordance with prior art does not lead to success.

One possible way to rule out external interference is offered by the evaluation of autocorrelation and cross-correlation functions of sensors which are positioned at a fixed distance from one another. The cross-correlation describes a correlation of two signals as a function of the time shift between these signals. In the case of autocorrelation, the correlation of a signal with itself is calculated. The autocorrelation function always has a maximum at displacement 0. If a signal with a delay is picked up by two otherwise equal sensors, the maximum of the cross-correlation function with an otherwise equal shape is displaced by the delay with respect to the maximum of the autocorrelation function.

One essential precondition for the identification of the passage of a capsule through the esophagus is that the sensor assemblies are able to detect a time-offset component of the signals. The problem which remains, however, is caused by the movement of the sensor assembly in the surrounding Earth's magnetic field, which certainly matters to the usability of the detector system according to the invention.

Figure 4:
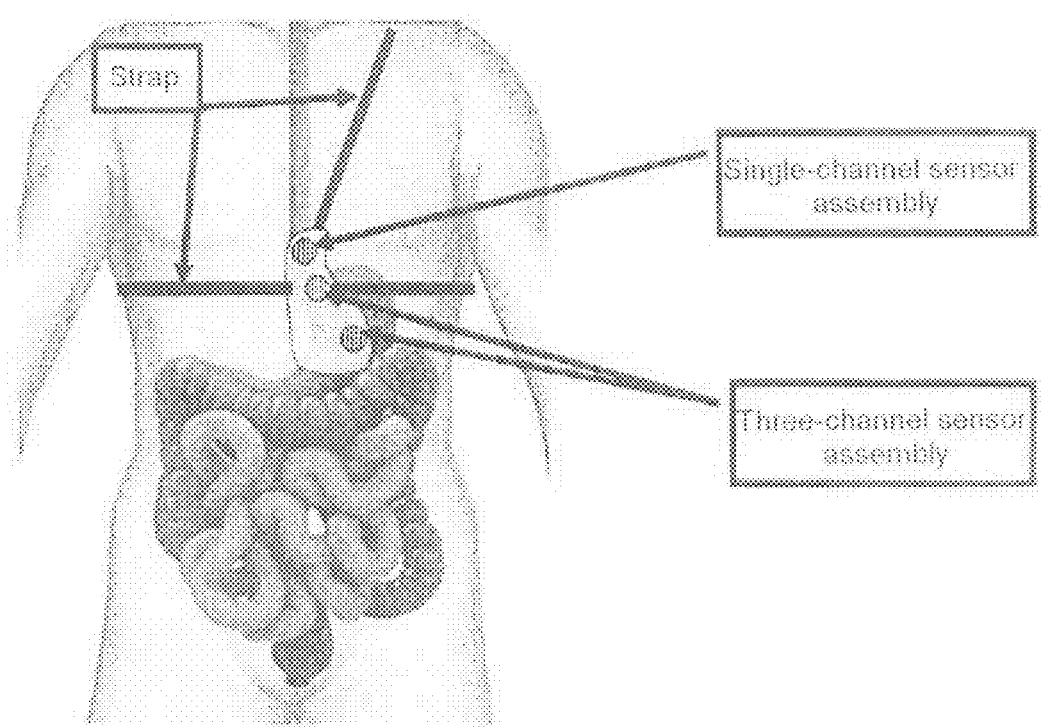

Surprisingly, it has been found that, despite a multiplicity of magnetic fluxes from numerous objects, for example from vehicles, metallic furniture, power-carrying lines and the like, such fluxes which originate from the magnetic body in the human organism are detected unambiguously by the detector system if the distance between two sensor assemblies is chosen to be from 2 to 6 cm. By means of unequal locations of the sensor assemblies, external magnetic fields which do not originate from the magnetic body in the human organism are detected. The sensor assemblies are preferably fixed vertically or horizontally over esophagus or breastbone and stomach. FIG. 4 shows the detector system according to the invention having three sensor assemblies in a combined breast and shoulder strap, worn on the person. In this exemplary embodiment, the sensor assembly in the vicinity of the esophagus has a single channel, on the other hand the two other sensor assemblies are implemented with three channels. The solely single-channel design of the sensor assembly in the vicinity of the esophagus simplifies the construction and reduces the power demand of the detector system according to the invention. In addition, this single-channel embodiment makes use of the possibility that the magnetic body does not have to be designed spherically symmetrically but, for example, can be designed cylindrically symmetrically, and the magnetic field generated by the same moves relative to the single-channel sensor assembly without rotating during the passage of the esophagus.

It can also be advantageous to remove the proportion of the interfering surrounding fields by means of the subtraction of a sliding average and to choose the distance between the sensor assemblies to be 2 cm. By using the filtered signals, the autocorrelation and cross-correlation functions thereof can then be calculated. By using the differences between the amplitudes and the position of the maxima, the passage of a magnetic body can then be detected.

If the detector system according to the invention has two or three sensor assemblies, it can also be used to detect the magnetic body in the stomach.

The slow disintegration of the magnetic body leads to the weakening of the magnetic flux density thereof. Movements of the wearer and positional changes of the magnetic body, for example as a result of peristalsis, lead to fluctuations in the measured value. Although, in general, no statements are possible about the superposed movement pattern of peristalsis and magnetic body, the detector system having three sensor assemblies leads to success. It is further advantageous to equip this detector system with low-pass filtering as a measure for signal processing.

The magnetic body of the detector system according to the invention can be embodied in such a way that it can be administered via oral ingestion, in particular swallowed by the person. The configuration of this magnetic body will also be called "oral administration form" within the context of the invention. This can be a capsule or a capsule with function, wherein the function is chosen from diagnostic and/or pharmacological form. The capsule can furthermore preferably be a tablet, which preferably passes the esophagus in the longitudinal direction. The administration form has at least one magnetic component, preferably a paramagnetic, super paramagnetic, ferrimagnetic and/or ferromagnetic component, preferably at least one core and/or shell containing magnetite. The magnetic component can have magnetically orientable or magnetizable particles, preferably magnetite ($Fe_3O_4$) or maghemite ($Fe_2O_3$). Magnetite and maghemite count as toxicologically and pharmacologically harmless and, amongst other things, are used as non-toxic, insoluble pigments in foodstuffs or pharmacological forms.

Optionally, other magnetically orientable particles such as ferrite $MnFe_2O_4$ or $MgFe_2O_4$ can also be suitable. The magnetic proportion of the magnetic body can lie in the range from 0.05 to 80 mg, preferably from 2 to 70, preferably 4 to 60, in particular 6 to 50 mg, of magnetically orientable or magnetizable particles. The average particle sizes of the magnetically orientatable particles can lie, for example, in the range from 1 nm to 1 mm, preferably from 100 nm to 100 μm.

The oral administration form can likewise preferably be a capsule, a tablet, a small rod, a coated tablet, a melt extrudate or body having an incorporated magnetic film.

Therefore, the detector system according to the invention, in which a sensor assembly is oriented orthogonally with respect to the main axis of the administration form, detects a marked change in the measured value during the passage of said administration form.

The time scale and the spatial scale on which the measured signals, at least from the two sensor assemblies, lie are given by the speed with which the oral administration form passes the detector system according to the invention, and by the spacings or pairwise spacings of the sensor assemblies. Although, as already stated above, a multiplicity of magnetic flux densities are superimposed and the actual flux density of interest is very small and inhomogeneous over time and space, it has been recognized that this can be detected reliably by the detector system according to the invention.

Therefore, a subject matter of the invention is likewise a method for detecting the magnetic flux density produced by a magnetic body in the human organism by means of the detector system according to the invention, which is characterized by the steps that (a) at least once, a set and reset pulse is connected up to each anisotropic magnetic resistance sensor, and
(b) the signals from each AMR sensor are amplified via suitable signal conditioning and via at least one low pass filter, and then
(c) the difference between the magnitudes of the vectors of the magnetic flux densities from each sensor assembly is determined, and/or the angle $\Phi$ between the vectors is calculated from the measured signals from the AMR sensors.

The method has the advantage of reducing dynamic interference during the detection of measured values. Specifically, if the magnetic field is distorted by external influences, for example by vehicles driving past, during the determination of the offset value, then those skilled in the art will obtain distorted offset values. A further danger of distortion is known by those skilled in the art as a result of the transient and decay behavior of filters that are used. However, we find that these effects are reduced by the method according to the invention.

In step (a), the set and reset pulses are applied alternately, which equally means that these are applied cyclically. They should be output with a current pulse intensity at which saturation magnetization is achieved in each case, and therefore the slope of the characteristic curve is controlled. The current pulse intensity fluctuates in a way known to those skilled in the art, depending on the component.

In step (b), Gauss filters, Bessel filters can preferably be used to suppress overloads or waviness in the signal. In order to separate fast and slow changes in the signals, band pass filters known to those skilled in the art are a preferred type of signal conditioning. Periodic electromagnetic interference having frequencies of 16.7 Hz, for example in the case of electrified rail operation, or 50 Hz, the mains frequency, can be suppressed by choosing the sampling rate and the integration time of 60 ms or multiples during the data acquisition. The integration time has to be matched accordingly in the event of differing frequencies of the periodic interference.

In order to filter out electromagnetic interference radiation from the frequency ranges from 16 to 50 Hz, preference is given to 2 arrangements, in which the integration constant is at least 60 ms. Preferably, in this way the sampling frequencies are matched to different periodically occurring interference sources.

The measure of the magnetic flux density in the x, y and z direction in step (c) is the voltages dropping in the respective direction from the detuning of the Wheatstone bridges of the AMR sensors. The person skilled in the art will assume that, in the difference $\Delta_0$ between the vectors from two sensor assemblies, $$\Delta_0 = S_1 - S_2,$$

the proportions of homogenous magnetic flux densities just cancel out. The influence of interfering external fields, barely variable in space, would therefore be compensated, and there would only remain substantially the field from the magnetic body in the wearer. However, the two sensor assemblies must not be tilted or tilted only a little with respect to each other, equivalent to the angle 0°. Magnetic flux densities of events offset in space and time are, however, surprisingly detected even at larger angles if, instead of $\Delta_0$, the scalar value $\Delta$ is formed:

$$\Delta = |S_1| - |S_2|$$

This simplifies the mounting of the sensor assemblies in the strap of the detector system according to the invention and, in addition, saves tedious adaptations in the position of the sensor assemblies to different proportions of the wearer. In a graph of the value $\Delta$ as a function of time, characteristic line forms are thus detected and, for example, are assigned to the swallowing of the magnetic body, the passage of the latter through the esophagus, thus the passage of the sensor assemblies, and the movement of the latter on account of the peristalsis during the digestion.

In order to be able to perform this assignment, the filtering of the measured signal is not adequate. Although the prior art knows one possible way of ruling out external interference by means of the evaluation of autocorrelation and cross-correlation functions of sensors which are positioned at a fixed distance from one another, if a signal with a delay is picked up by two otherwise equal sensors, the maximum of the cross-correlation function with an otherwise equal shape is displaced by the delay with respect to the maximum of the autocorrelation function. In order that a time offset between autocorrelation and cross-correlation of the sensor signals can now be detected, the proportion of the signal caused by the oral administration form must not be covered by external magnetic fields. To this end, however, the external interference would largely have to be eliminated. For this purpose, for example, the formation of the difference between the current signal and an average is used. This average must be matched to the current situation and, for example, be obtained as a so-called "moving average". However, this means that, during the ingestion of the oral administration form, the test person completes neither rapid rotational nor rapid translational movements of large amplitude. Only then will sensors according to the prior art ensure adequate signal separation.

Of course, the sampling rate can also be increased, so that a continuous measurement would be implemented without any overloads. It is possible to compensate, at least partly, for the disadvantage of an energy demand that would then be increased, by high sampling rates only being set in the case of interesting, complex events, such as for example during swallowing and/or the disintegration of the magnetic body. Such interesting, complex events must be detected by the system, however. The detector system according to the invention has an advantageous embodiment in which interesting, complex events are detected, specifically by using the registration of the exact time of the ingestion. This embodiment will be explained further below. In solutions according to the prior art, however, there is further the problem that rapid rotational and/or translational movements of large amplitude which do not correlate with the oral administration form continue to be visible in the measured signals.

Surprisingly, the alternative calculation of the angle $\Phi$ enclosed by the measured signal vectors in accordance with the formula I, $$\Phi = \arccos(S1 \cdot S2/|S_1||S_2|), \quad \text{I}$$

in step (c) of the method circumvents this problem. We found that rapid movements of the wearer and/or rapid external flux changes of the interfering fields act less significantly on the relative orientation of the measured signal vectors in relation to one another than the movement of the magnetic body in the carrier organism. This can be explained by the sources for external flux changes deflecting both the measured signal vectors or, in the case of three sensor assemblies, three measured signal vectors, in at least approximately the same directions. Although the magnitudes thereof can quite possibly change differently, the angle between two pairs of the measured signal vectors in each case, based on the time, must remain approximately the same. This is the equivalent to the surrounding magnetic field from further removed sources approximately maintaining its homogeneity or inhomogeneity. I accordingly permits magnetic fluxes from further removed sources to be masked out, irrespective of their time behavior.

Figure 3:
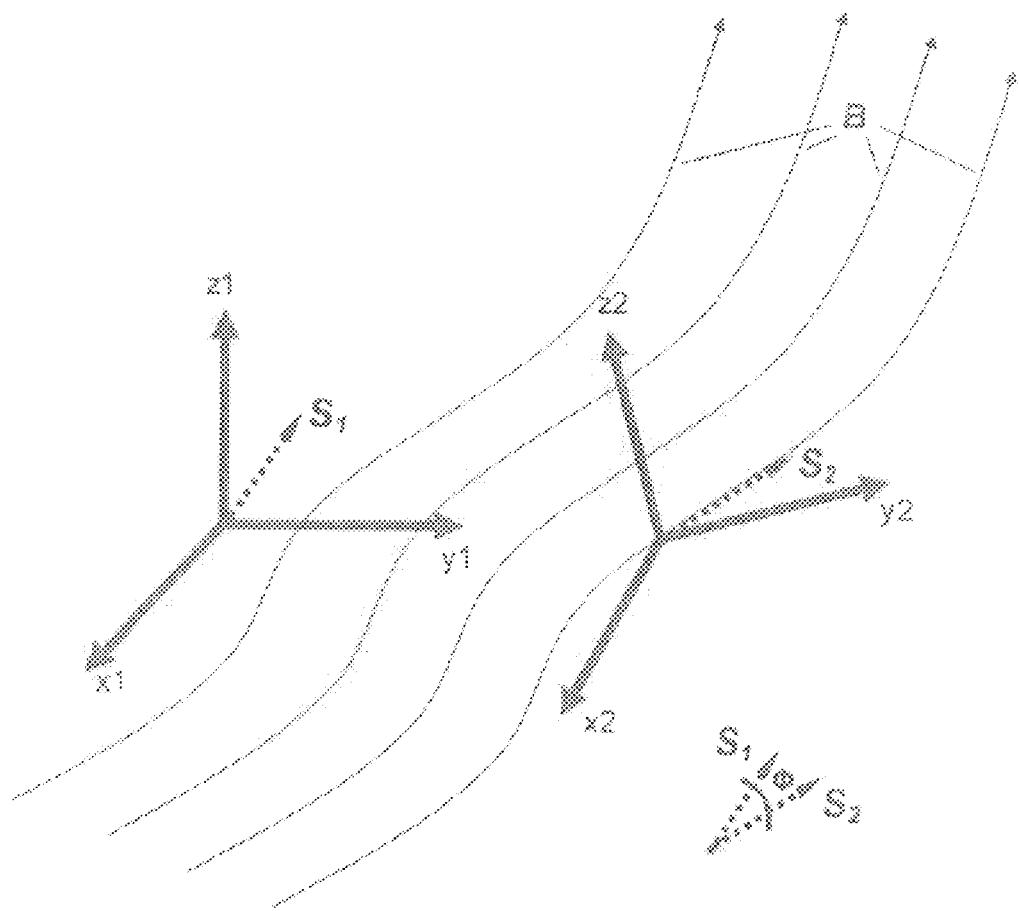

The situation during the performance of the method according to the invention is shown schematically by FIG. 3. The indicative symbols mean:
B Field lines of the interfering magnetic flux
$S_1$, $S_2$ Vectors $S_1 = (S_{x1}, S_{y1}, S_{z1})$ and $S_2 = (S_{x2}, S_{y2}, S_{z2})$
$\Phi$ angle enclosed by the measured signal vectors in accordance with formula I.

Under the assumption that sources of the interfering magnetic flux are physically further removed than the magnetic body or the oral administration form, the angle between the vectors $S_1$ and $S_2$ is approximately constant over time. In the best case, namely in a homogenous magnetic field, this angle even disappears constantly. However, it has been found that interfering magnetic fields are often substantially homogenous. One advantage during the determination of the angle $\Phi$ is the unimportance of erroneous orientation of an individual AMR sensor or all the AMR sensors or the tilting of the sensor assemblies with respect to one another, if this erroneous orientation is constant over time. Such an error manifests itself in an insignificant offset in the $\Phi/t$ graph, equivalent to $$\Phi = \text{const}$$

with respect to the time t.

In the method according to the invention, in step (b), it is possible to use at least one low pass filter having the cut-off frequency of 0.1-0.99 mHz, 1 mHz-0.99 Hz, 1 Hz-9.99 Hz, 10 Hz-1 kHz, or a combination of low pass filters having at least two different cut-off frequencies. In this case, it is preferable to adapt the filtering to the process to be detected, in order to suppress noise and/or rapidly changing interference fields, for example from electrical appliances, in the measured signal.

In the method according to the invention, the magnitude of each AMR sensor or the measured signal obtained in step (c) can be filtered by a median filter.

Furthermore, in the method according to the invention, during the performance of step (c), the variable $\Delta$ and/or $\Phi$ that is obtained can be recorded as a function of time by means of a data logger or another suitable device known to those skilled in the art, with which the detector system according to the invention can be equipped. This recording can be carried out continuously, for example during the ingestion, the passage and/or the disintegration of the magnetic body in the organism of the wearer. It can also be carried out discontinuously, in order for example to save energy.

It was found that many everyday sources of interfering fields produce characteristic line forms in the $\Delta$/t or $\Phi$/t graphs. Thus, for example, motor vehicles travelling past, electrical switching operations, electromagnetic interference caused by sparks and also stochastically periodic interference and/or brush sparking from electric motors can be detected in the graph and it is possible to compensate for the contribution thereof to the line form by means of software known to those skilled in the art.

The method according to the invention can advantageously also be used when the magnetic body is already located in the stomach and disintegrates there. The magnetic body can also disintegrate in the intestines or in the colon. In these cases, digital filtering in the range from 0.1 to 1 mHz is preferred. If the swallowing operation is to be detected, a low pass filter having a cut-off frequency range from 1 mHz-0.99 Hz is preferred. Furthermore, it can be advantageous to adapt the choice of filters and/or cut-off frequencies to the geometric structure of the magnetic body, in particular the oral administration form. The time period in which an oral administration form, for example a capsule (FIG. 10), disintegrates lies in the range from 0.5-30 min, preferably in the range from 0.5-20 min, further preferably in the range from 0.5-5 min. If such long-lasting processes in the human body are to be measured, the signals can preferably be "smoothed exponentially". The mathematical procedure for this is known to those skilled in the art. Preferred smoothing constants $\alpha$ lie in the range from 0.10 to 0.40; particularly preferably a is approximately or equal to 0.25.

The magnetic body of the administration form of the detector system according to the invention has subunits, which can be layers, phases and/or domains. That subunit which produces the magnetic flux has inert, crystalline particles, which can be particles, glazed and/or encapsulated micro and/or mini magnets. The micro and/or mini magnets preferably have the form of cylinders, shells and/or spheres.

Preferred dimensions of the micro or mini magnets are from 0.1 to 1 µm, from 1 to 10 µm, from 10 to 100 µm, from 100 µm to 1 mm, and/or from 1 mm to 10 mm. The micro or mini magnets have magnetic particles, preferably those made of magnetite and/or a magnetic material which does not metabolize with the human organism. Furthermore, the magnetic particles can have micro-structured polymer composites and/or partially crystalline, polymorphic, sintered, powdery or combinations thereof. The magnetic particles can also have further commercially common components, preferably coated by the latter, for example by dextran particles, or by other components for molecular coating, for example by cyclodextrins, or by components which are obtained by granulation or pelleting methods. If the micro or mini magnets are encapsulated or coated by means of the latter, the systematic absorption of the micro or mini magnets is inherently hindered. Preferably, the disintegration of the micro or mini magnets by the stomach acid is slowed by these and/or the start of the disintegration is retarded. With the progressive disintegration, in turn that magnetic flux weakens until it disappears, which is registered by the detector system according to the invention in accordance with the method of the invention. FIGS. 5A, 5B and 5C show preferred embodiments of the magnetic body, specifically in the form of a capsule, which is respectively equipped with one (FIG. 5A), two (FIG. 5B) or three (FIG. 5C) mini magnets (m).

The magnetic body is preferably produced by means of galenic methods known to those skilled in the art for the production of oral administration forms, for example by means of GMP-capable production methods, preferably for the production of granules by means of a so-called high shear mixer, or in a fluid bed granulator, by means of a roller compactor, an extruder, spheronizator or a hot-melt process. Also preferred is the production of so-called pellets by means of pelletization known to those skilled in the art, extrusion and spheronization, rotary granulation or powder layering. Furthermore, magnetic bodies can be produced in the form of micro tablets from partially crystalline, compressed, coated and/or tableted material, by these being compacted from powder and polymorphic substances. Oral administration forms can also be produced in the form of small envelopes known to those skilled in the art, so-called sachets.

Also conceivable are more complex forms of magnetic bodies, in which, for example, the magnetic component has the form of one or more films. Magnetic bodies of the detector system according to the invention can be obtained in any desired combination of the above-mentioned methods. These can also be multi-particle systems, multi-layered systems, core-shell systems and/or co-block systems.

The oral administration form can have any desired form which has at least one magnetic phase, "magnetic phase" being understood to mean a body delimited physically in the magnetic body which causes a magnetic flux. The latter is detected in accordance with the method of the invention. The oral administration form, following ingestion into the human body, disintegrates in a defined time period. If, for example, two, three, four or five magnetic phases are contained, these time periods can have different lengths, preferably different lengths in pairs. The different lengths of the time periods can be achieved, for example, by the magnetic material being coated in a polymer film.

If the oral administration form is a capsule, for example half the capsule can be filled with the magnetic material. Furthermore, the magnetic material pressed into a tablet can be put into the capsule. The magnetic phase can preferably be surrounded by a sheath which is resistant to stomach acid and which coincides with the sheath of the oral administration form or is different from the latter. The function of such slowly disintegrating sheaths, also called "coatings" or "matrix structures", is known to those skilled in the art. With the start of the disintegration of the sheaths, the disintegration of the magnetic material obviously also begins as soon as the latter comes into contact with the medium which effects or has effected the disintegration of the sheath. With the disintegration of the magnetic material, the collective ordering of the electron spin causing the magnetic flux is lost and, with the extinguishing of the collective magnetic ordering, the magnetic flux weakens as far as its inability to be measured or its disappearance.

The material of a slowly disintegrating sheath or encapsulation can be chosen from film-forming polymers. These can be, for example, copolymers of methyl methacrylate and ethyl acrylate, copolymers of methyl methacrylate and ethyl acrylate and methylacrylic acid, copolymers of methyl methacrylate and methyl methacrylate and methacrylic acid and copolymers of methyl methacrylate, ethyl acrylate and trimethylammonium ethyl methacrylate.

Suitable in particular are copolymers of the type EUDRAGIT® E100, EUDRAGIT® E PO, EUDRAGIT® L100, EUDRAGIT® L100-55, EUDRAGIT® S, EUDRAGIT® FS, EUDRAGIT® RS or EUDRAGIT® RL. EUDRAGIT® NE or EUDRAGIT® NM.

Also suitable are polyvinyl pyrrolidone (PVP), polyvinyl alcohols, polyvinyl alcohol-polyethylene glycol graft copolymers (Kollicoat®), starches and derivatives thereof, polyvinyl acetate phthalate (PVAP, Coateric®), polyvinyl acetate (PVAc, Kollicoat), vinyl acetate-vinyl pyrrolidone copolymers (Kollidon® VA64), vinyl acetate: crotonic acid copolymers, polyethylene glycols with a molecular weight above 1000 (g/mol), chitosan, a (meth)acrylate copolymer, consisting of 20-40% by weight methyl methacrylate and 60 to 80% by weight methacrylic acid, known as is EUDRAGIT® S, a crosslinked and/or non-crosslinked polyacrylic acid, fissure sealer known as Smartseal® based on a composite, salt of alginic acid and/or a pectin, celluloses such as, for example, anionic carboxymethyl cellulose and salts thereof (CMC, Na-CMC, Ca-CMC, Blanose, Tylopur), carboxymethyl ethyl cellulose (CMEC, Duodcell®), hydroxyethyl cellulose (HEC, Klucel), hydroxypropyl cellulose (HPC), hydroxypropyl methyl cellulose (HPMC, Pharmacoat, Methocel, Sepifilm, Viscontran, Opadry), hydroxymethyl ethyl cellulose (HEMC), ethyl cellulose (EC, Ethocel®, Aquacoat®, Surelease®), methyl cellulose (MC, Viscontran, Tylopur, Methocel), cellulose ester, cellulose glycolate, cellulose acetate phthalate (CAP, Cellulosi acetas PhEur, cellulose acetate phthalate, NF, Aquateric®), cellulose acetate succinate (CAS), cellulose acetate trimeliate (CAT), hydroxypropyl methyl cellulose phthalate (HPMCP, HP50, HP55), hydroxypropyl methyl cellulose acetate succinate (HPMCAS-LF, -MF, -HF) or is a mixture of the aforementioned polymers.

In addition to the film-forming polymers, further pharmaceutically usual aids which are not film-forming polymers can be used in a known way as formulation aids or additionally contained. Here, stabilizers, colorants, antioxidants, wetting agents, pigments, glossing agents, etc. can be named by way of example. They are primarily used as processing aids and are intended to ensure a reliable and reproducible production method and good long-term storage stability. Further pharmaceutically usual aids can be present in quantities from 0.001 to 30, preferably 0.1 to 10% by weight, based on the film-forming polymers. Likewise, additives known to those skilled in the art for tablets, capsules or pharmacological forms can be employed.

The oral administration form can furthermore have a least one shell and at least one core, which are the magnetic phases and which are disintegrated from outside to inside in order in the human organism, so that the core or the cores maintains or maintain the magnetic flux for the longest.

For example, the administration form can have a core in the form of a flat tablet, wherein the flat sides of the tablet are the magnetic phase, which is firmly connected to a further substance, for example fixed chemically or mechanically or fused, and which is intended to be supplied to the human organism. This substance can be, for example, an active substance, a drug or generally a biologically active substance and be present on the inside of a magnetic shell. The magnetic phases of the tablet can have various thicknesses or be coated in various ways by a further material, wholly or partly, so that the magnetic phases disintegrate within time periods of different lengths. These time periods can be chosen such that the magnetic phases disintegrate while the administration form is being transported in the human organism, and thus each magnetic phase disintegrates at a different location in the human organism. For example, a time period can be chosen to be short, with the result that one of the magnetic faces disintegrates as early as during the passage through the esophagus.

In a further preferred embodiment, the oral administration form can have at least three constituent parts, of which at least one constituent part, preferably each constituent part, encloses a magnetic phase.

The oral administration form can, moreover, have at least three phases, of which at least one phase can have a biologically active substance, and the other phases contain no biologically active substances but one or in each case one magnetic phase. Such administration forms can be produced more simply.

The oral administration form can likewise preferably have a magnetic phase at or on its outer surface. When such an administration form is ingested, the magnetic phase disintegrates first. Only after that do the remaining constituent parts of the administration form come into contact with the human organism. This embodiment has the advantage, not exclusively, that the detector system according to the invention is able to register the exact time of the ingestion. The exact time of the ingestion can be detected, for example, by a peak in the time derivative $\partial \Delta/\partial t$ of the measured signal vector difference and/or in a sudden rise in the magnitude of $\partial \Phi/\partial t$ above a value which has previously been defined. Within the context of the invention, such a time is equivalent to the detection of changing magnetic fields and thus the detection of the esophagus passage.

Figure 6A:
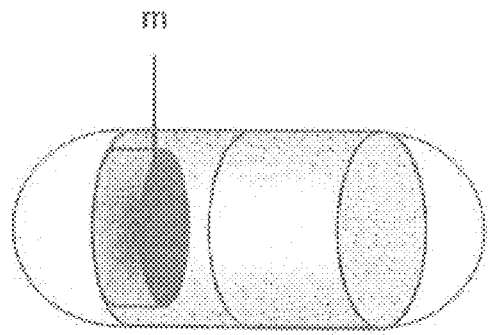
Figure 6B:
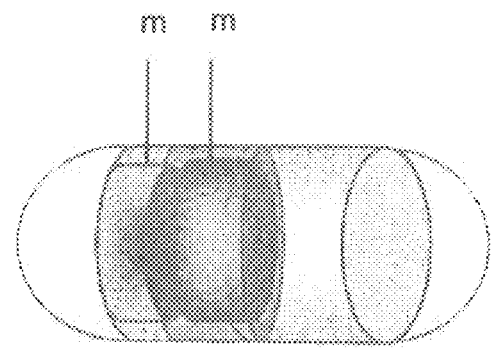
Figure 6C:
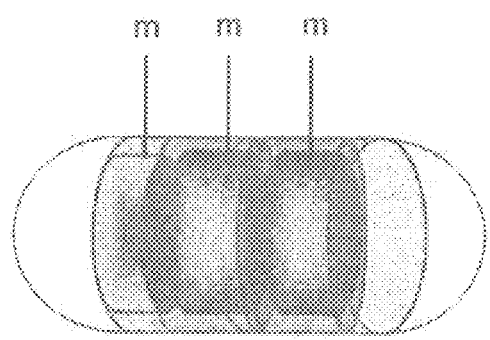
Figure 6:
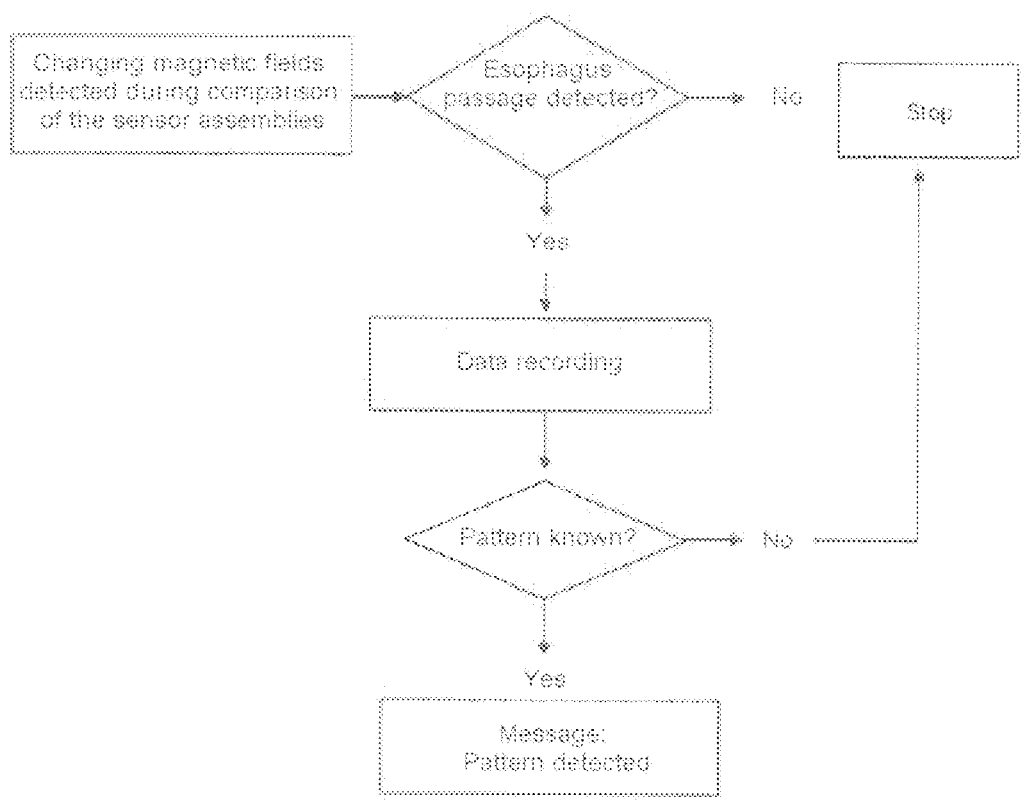

If the detector system according to the invention is equipped with a device for recording the variable $\Delta$ and/or $\Phi$ as a function of time, the detection of the esophagus, designated by "esophagus passage detected" is logically positive. The processing of this and of the following logical state is illustrated schematically in FIG. 6.

If, on the other hand, the time of ingestion is known, it was found as a further advantage of this administration form that various external magnetic fluxes or flux changes which are present at various times and cannot be masked out or calculated out completely in step (b) and/or (c) are nevertheless detected as interfering fluxes, by the line form respectively generated in the $\Delta/t$ or $\Phi/t$ graph by the magnetic flux of the administration form following the ingestion time being used as a respective characteristic for the graph. This can be brought about in that, directly after the first-time ingestion of the administration form, the line form is tabulated during a time interval of 0 to 10 s, preferably from 0 to 5 s, and/or is approximated by suitable mathematical functions. Immediately after each further ingestion, at respectively known times, the line form then detected can be compared with the tabulated or approximated line form. Within the context of the invention, such a comparison is designated by "data recording and data comparison". If the line form detected coincides in its tabulated and/or approximated form with the line form during the first ingestion of the administration form, then this finding, designated by "pattern known", is logically positive. If the logical values esophagus passage detected and pattern known are positive, the detection according to the method of the invention can be performed, since that which is measured by means of the changing magnetic fields is "pattern detected". Then, however, the further flux changes, which cause the passage of the administration form and the disintegration of the latter in the organism, are detected during various times of the ingestion, despite different surroundings. This results in the further advantage of mobility of the detector system according to the invention, virtually irrespective of the location or intensity of external magnetic fluxes, since the method according to the invention now even distinguishes between various, unknown external interfering influences. If at least one of the two logical states is negative, the detection can be avoided, the detector system according to the invention can be switched off and/or a further message, which is matched to the use of the system, can be generated.

The subject matter of the invention is therefore likewise the use of the detector system according to the invention for detecting swallowed oral administration forms and for determining the time or times of the disintegration of the magnetic, preferably ferromagnetic, component in the digestive tract. The advantage consists in the fact that, at the time at which this component disintegrates, or a defined time period before the same, the magnetic body, generally the oral administration form, likewise disintegrates or must disintegrate, and thus substances enclosed therein must be liberated. The detection of the disintegration can thus be a time marker for when, for example, an active substance reaches a specific part of the human organism.

Preferably, during the use according to the invention, the disintegration of the magnetic, preferably ferromagnetic, component in the stomach, large intestine, small intestine and/or colon can be determined. One option of the use according to the invention is as follows.

If the magnetic body has at least two magnetic phases, the disintegration times of which are chosen such that these magnetic phases disintegrate at different locations in the human organism and, in addition, in each case a substance which can be taken up by the human organism and, for example, can be an active substance, a drug or generally a biologically active substance, is firmly connected to each of these magnetic phases, and, with the detection of the respective disintegration, in addition a measurement of the blood level of the substance or substances taken up by the organism is carried out, then, for example in clinical studies, the output of this substance or these substances can be correlated in vivo with the behavior of the metabolism. The detector system according to the invention can accordingly also be used in therapy and/or diagnostics. The substance taken up by the body can also be a food and stimulant, and thus the detector system according to the invention can be used in all areas of nutrition.

During the use according to the invention, the measured signals obtained in accordance with the method of the invention can be stored in a data storage device, and the stored data can preferably be transmitted to a receiving device upon the receipt of a request signal.

The detector system can preferably transmit the signals via a commercially available Smartphone, cell phone, PDA, wherein conditioning of the signals can be carried out by a further algorithm on board this small computer. One example of such conditioning can be data reduction, encryption and/or reconciliation with personal data of the wearer. The signals obtained from the detector system according to the invention can be transmitted on a cable-bound path, for example temporarily by means of a plug-in connection, and/or in a wire-free manner, for example via sensor nodes, computers or by means of Bluetootetechnology to a mobile telephone. If this technology is used, the expenditure for porting the software to the digital signal processor (DSP) can be saved and the processing time can also be shortened.

The data storage device can be a data logger with transmitter which, for example, can be implemented in Bluetooth® technology. It is likewise conceivable to equip the detector system according to the invention with a data logger with transmitter, or else with a "radio-frequency identification device" (RFID). By means of such a circuit, simply structured information can preferably be transmitted and received, for example that data which can be linked with a special event, for example an emergency, can be transmitted. This information can preferably be derived from the measured signals, for example in the event of misuse, maladministration, excessively frequent or excessively infrequent dosing, under-dosing or overdosing of the oral administration form, energy emergency in or failure of the detector system. It is also possible to combine systems which are already applied in medication, such as implanted analgesic pumps or external perfusors, which control a monitored injection of pharmacological forms and wherein, under certain circumstances, a combination with further pharmacological forms should be avoided.

The receiving device can be any receiving device known to those skilled in the art which is supported by a public or non-public server, computer and/or network. The data received can be processed via a network comprising mobile radio devices, computers, workstations, small computers or any other computer or server, which conditions and/or stores this data, particularly preferably for the purpose of medical care. It may further be advantageous to use the detector system according to the invention in a public or non-public data management network, likewise preferably in data management or in a data management network within the context of therapy and/or diagnostics.

The data management network can be called up or used by experts. If, for example, an emergency is signaled, an expert, for example an emergency doctor, can be requested via an automated system, e.g. via a "computerized physician order entry system" (CPOE). The expert correlates the data collected by the data management network, in order to determine the location and time of the event, e.g. of the emergency, and in order to take suitable measures.

If the detector system according to the invention is used in therapy and/or diagnostics in accordance with the invention, the data management network can advantageously be equipped with a pharmacy computer or a pharmaceutical database, likewise advantageously with an expert system for medication.

The signals obtained by the detector system according to the invention and optionally transmitted can be processed, encoded and/or transmitted into the data management network in packed form. The data transmitted into this data network can be called up in a commercial route by means of a telephone call. The data transmitted can log the time-resolved disintegration of the magnetic body indirectly or directly, in real time and/or stored form, confirm said data or trigger further input requests in a manner known to those skilled in the art.

Data management networks for therapy and clinical developments are known and, by using expert systems, which are for example neural learning algorithms, produce higher data qualities and categories than the sum of the individual data. Higher data qualities from large statistical totals can be obtained, for example, on the basis of data reduction or maximum entropy algorithms.

When using the detector system according to the invention and/or when using the method according to the invention in network systems, it is possible in particular to protect critical patients or individuals requiring care against misuse, erroneous application or other dangers in connection with the application of the magnetic body.

The detector system according to the invention can be used within the context of treatments, examinations, diagnoses and when researching new therapies and diagnoses, and within the context of linking medical technical systems.

Likewise, the detector system according to the invention can be used during the performance and monitoring of gastro-intestinal active substance dosing, in particular in solid or solid-liquid combined preparations.

Furthermore, it may be advantageous to use the detector system for high throughput tests. With the aid of such tests, the integrity of the magnetic layers, phases and/or domains can be tested, and also their time behavior during the dissolution in the human organism can be determined.

The invention will be explained below by using examples.

EXAMPLES

Comparative Example

Figure 7:
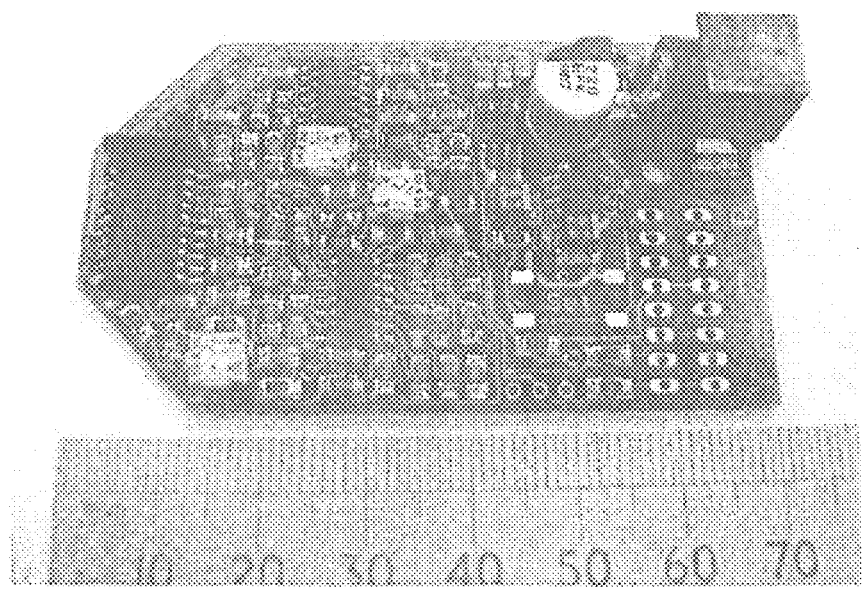
Figure 8A:
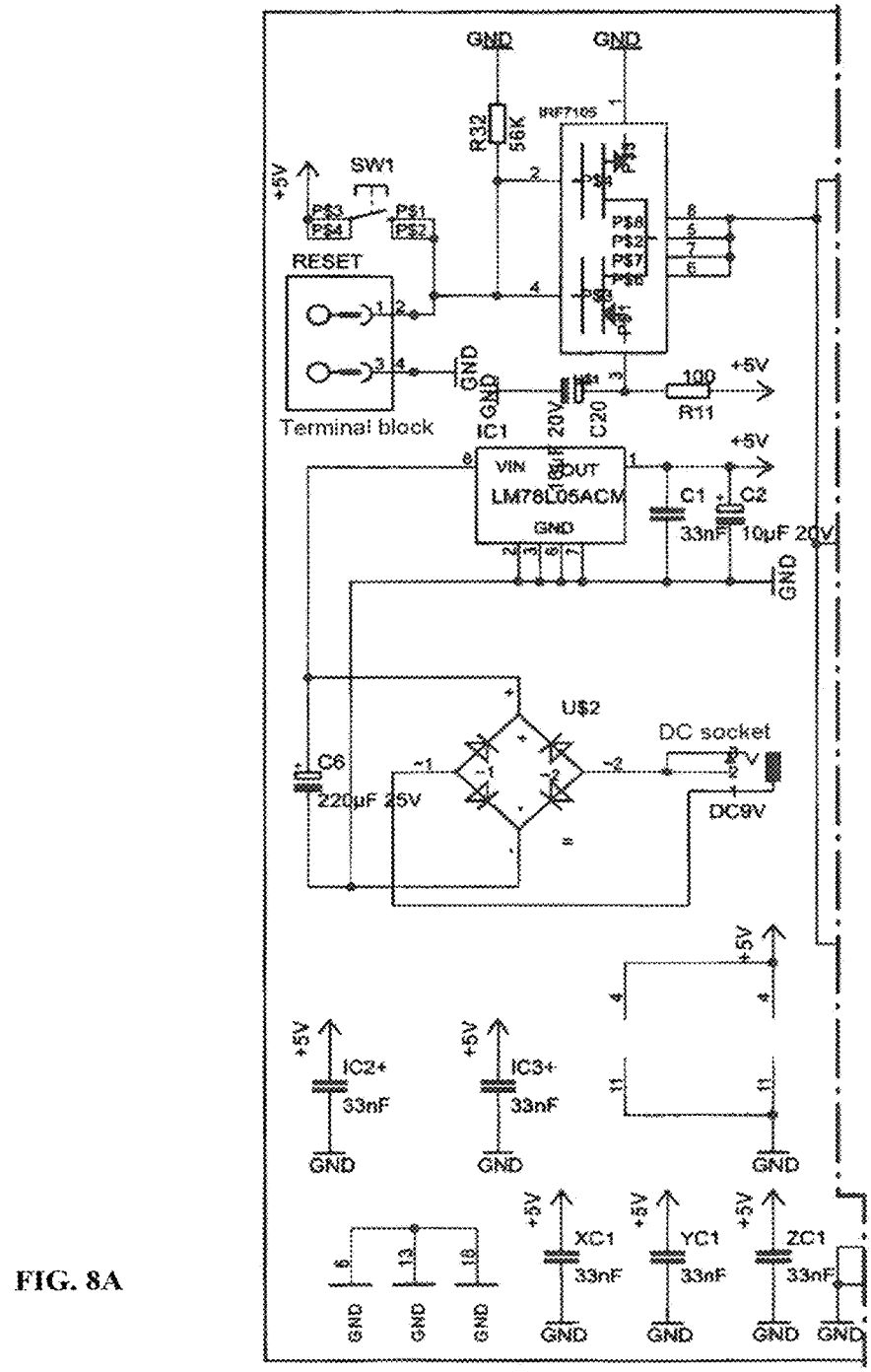
Figure 8B:
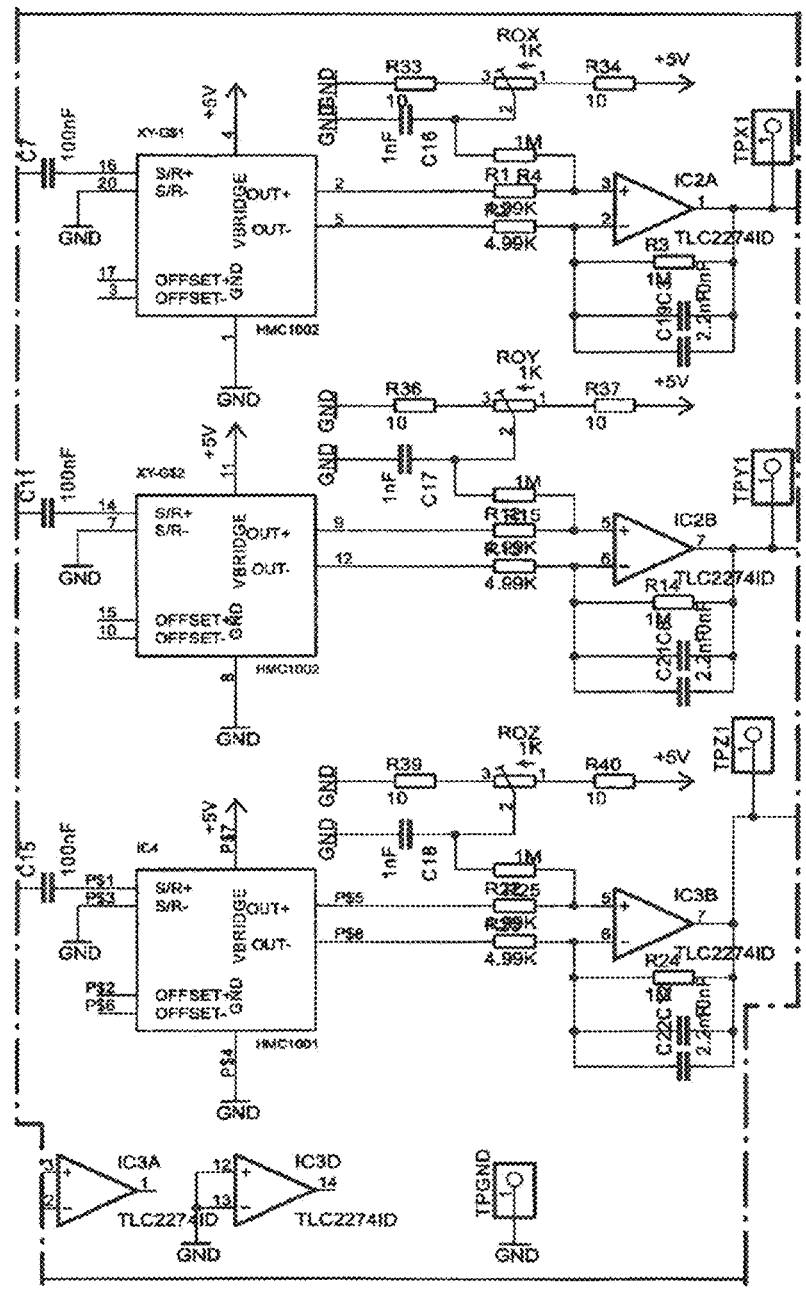
Figure 8C:
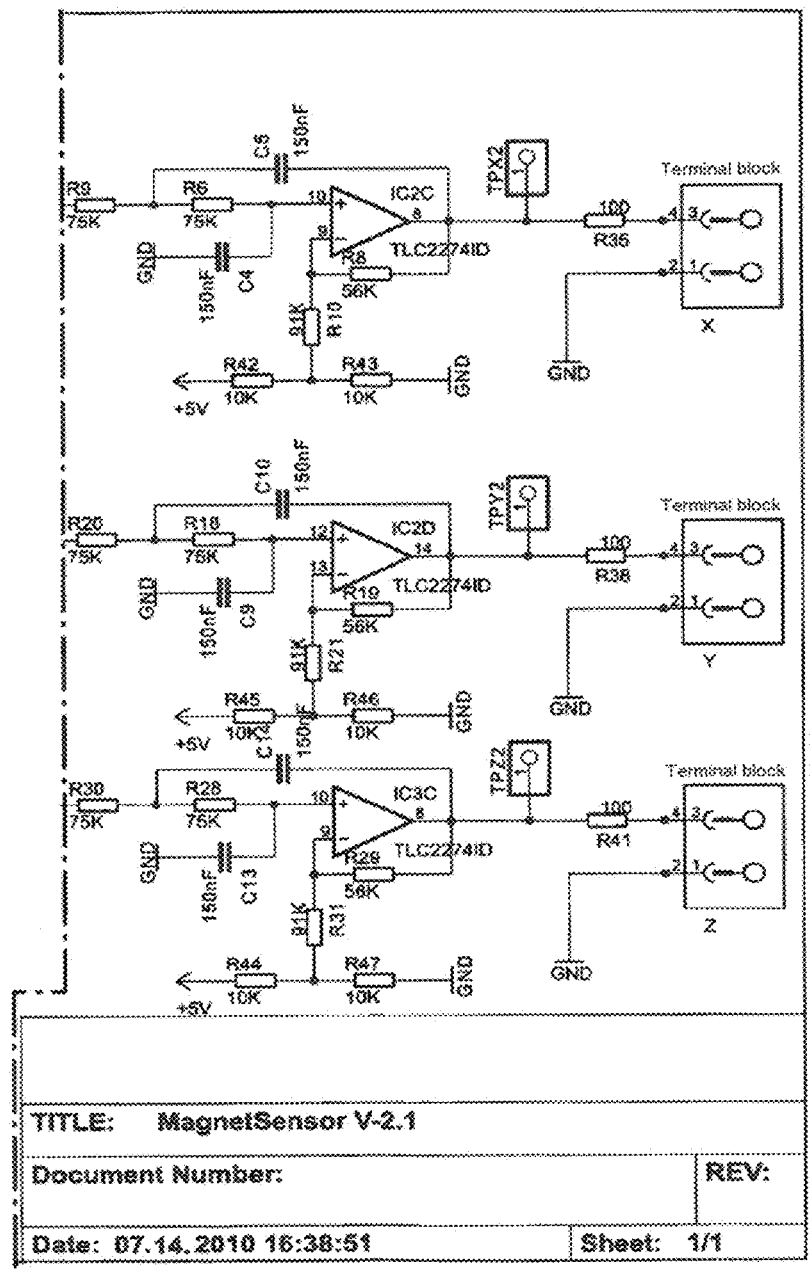

A sensor assembly having three AMR sensors was provided. FIG. 7 shows a photo of this arrangement. On the left-hand side, the AMR sensor circuits are to be seen, of which the axes of weak magnetization were located parallel to the printed circuit board plane and perpendicular thereto. The circuit diagram of the arrangement is illustrated in FIGS. 8A, 8B and 8C. The AMR sensors used also had, in addition to the actual sensor bridge circuits, two internal coils per axis.

The circuit illustrated operated without any offset strap and in a purely analog manner with a supply voltage of more than 7 V. Digitization and signal processing were carried out externally via a laptop with connected USB multi 10 subassembly of the type NI USB-6211, and by means of software from LabVIEW. Working point and offset adjustment had to be carried out manually via potentiometers. Only by omitting the offset strap could a low power demand be made possible.

This variant was unusable or at least cumbersome for mobile use on the human wearer, which had to last for several days, since working point and offset adjustment had to be performed manually again and again.

Example 1

(a) Capsule with Magnetic Body

First of all, the magnetic body was produced. The material:
hard gelatin capsules, size "0"
d-Fructose
magnetite
EUDRAGIT® FS 30 D
HCl 0.1 N The mini magnets (FIGS. 5A, 5B and 5C, m) were implemented as tablets containing magnetite, called "magnetite tablets" within the context of the invention. They were obtained by magnetite, maize starch, magnesium stearate and collidon first being mixed with one another in the way known to those skilled in the art. The mixture was then pressed to form tablets in a manner likewise in accordance with the prior art. These tablets were provided with a base coating and then equipped with a further functional coating, which delayed the disintegration of the magnetite tablets during a defined interval upon contact with the stomach acid.

The functional coating was composed of a mixture of sodium lauryl sulfate, stearic acid, talc and dibutyl sebacate and EUDRAGIT® E PO in proportions known to those skilled in the art. With the aid of a commercially available drum coater, the dispersion was applied over a time period of a few minutes up to some hours to the magnetite tablets previously provided with hydroxypropyl methyl cellulose (HPMC) as base coating. The longer this time period was, the thicker the coating became. The quantity of said coating applied is specified in mg.

The thickness of the coating achieved was critical for the time period during which the coated magnetite tablets resisted their disintegration by the the stomach acid. With the aid of different thicknesses of the functional coating, the retardation of the disintegration of the magnetite tablets and thus the disappearance of the magnetic flux of the latter could thus be configured differently.

Half a hard gelatin capsule was filled with a spatula tip of fructose. By using a fine pipette, 5 µl EUDRAGIT® FS 30 D were applied in the center of the tablet as a drop on a magnetite tablet. With the aid of forceps, a second magnetite tablet was placed congruently on the side of the tablet having the EUDRAGIT® drop and allowed to dry for about 10 min, the two tablets bonding.

The bonded tablets were placed with the aid of forceps into the half of a hard gelatin capsule, on the fructose powder. This half was filled with fructose and the powder compacted with occasional tapping. A spatula tip of fructose was put carefully into the second half capsule. The two half capsules were then plugged into each other, so that as little fructose as possible fell out.

Figure 9:
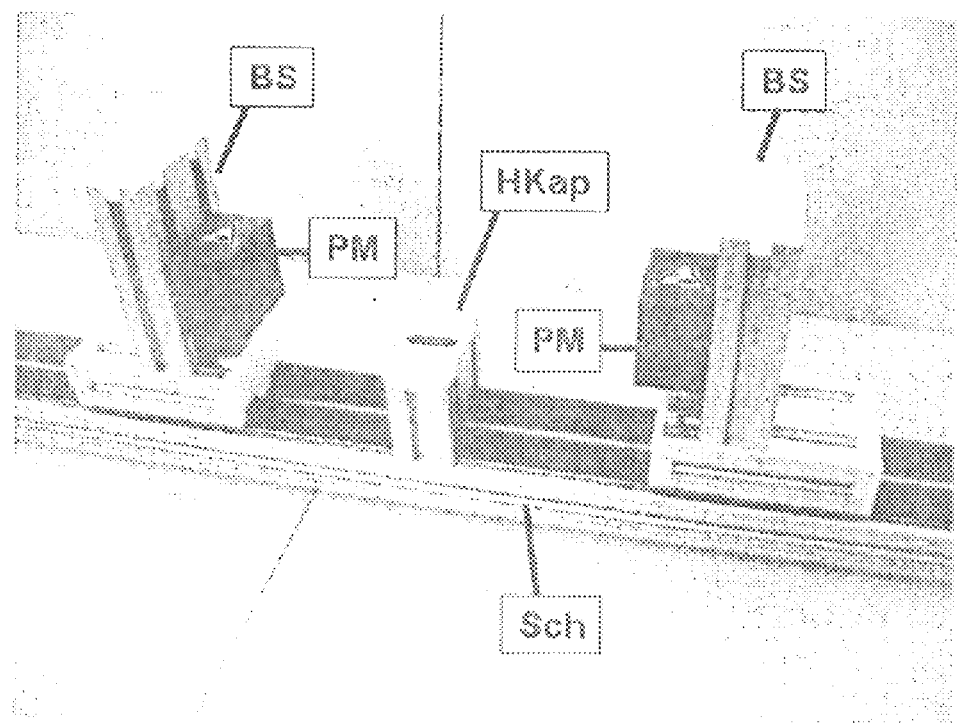

The internal structure of the capsule obtained in this way was documented and placed in a magnetization device. FIG. 9 shows a photograph of this device. The hard gelatin capsule provided with the magnetite tablets was positioned on the mount (HKap) such that the longitudinal axis of the hard gelatin capsule was parallel to the rail (Sch). Then, the two movable carriages (BS), which were equipped with permanent magnets (PM) and the magnetic fields of which were oriented parallel (North-South, North-South) to the rail, were pushed up to the mount having the capsule. As a result, the magnetite tablets were located in the resultant magnetic field and were given a magnetization oriented parallel thereto. It was found that, after a residence time of at most 5 min, saturation of the magnetization was achieved and was maintained permanently during the storage technically usual for magnetic materials and oral administration forms. In this way, a magnetic body according to FIG. 5 B was obtained.

If an antiparallel orientation of the magnetic fields of the magnetite tablets is desired, each magnetite tablet can also be magnetized individually in the device just described. Then, the magnetite tablets can be bonded with their magnetic poles placed oppositely and with the aid of forceps, placed into the half of a hard gelatin capsule, on the fructose powder, and the magnetic body then being assembled. Given this orientation of the magnetite tablets, however, de-magnetization phenomena are to be feared.

(b) Simulation Model

Figure 10:
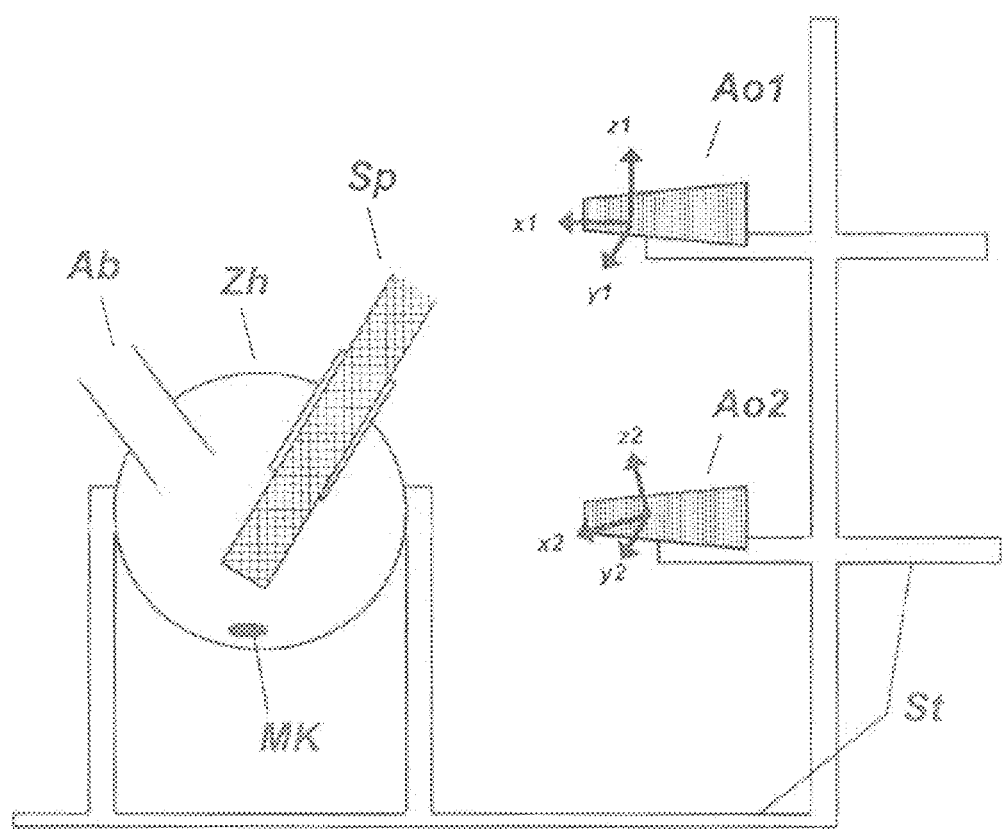

Furthermore, a simulation model, which is shown schematically in FIG. 10, was prepared. A two-necked flask (Zh), which simulated the human stomach, was filled with 300 ml 0.1 N hydrochloric acid, the temperature of which was thermostatically controlled to 37° C.

The feed to the two-necked flask simulated the esophagus (Sp). An air stream, which kept the liquid and the magnetic body (MK) moving gently, was led via this feed and the discharge (Ab), said liquid and the magnetic body being allowed to slide into the flask (Zh) through the esophagus (Sp) within the context of the examples. This movement was a simulation of the human movement and the peristalsis of the stomach.

Thermostatic control, filling and conduction of an air stream are not shown in FIG. 10. Of the detector system according to the invention, the figure shows only the two sensor assemblies (Ao1) and (Ao2). Both sensor assemblies were implemented with three channels, and FIG. 10 shows the two arrangements together with each of the axes of the weak magnetization x1, y1, z1 and x2, y2, z2. Via a stand (St), which replaced the function of the strap or an appliance carried on the person, two-necked flask and sensor assemblies were kept in position in relation to each other, and a defined spacing of 10 cm and a defined angle of about 0° between the two sensor assemblies was achieved. This simulated the wearing of the detector system according to the invention on the person.

The magnitudes of the vectors $S_1$ and $S_2$ of the sensor assemblies according to the invention were determined and subtracted from each other. However, before this could be carried out, each sensor assembly had firstly to be adjusted and calibrated.

(c) AMR Sensors and the Adjustment and Calibration Thereof

Figure 11:
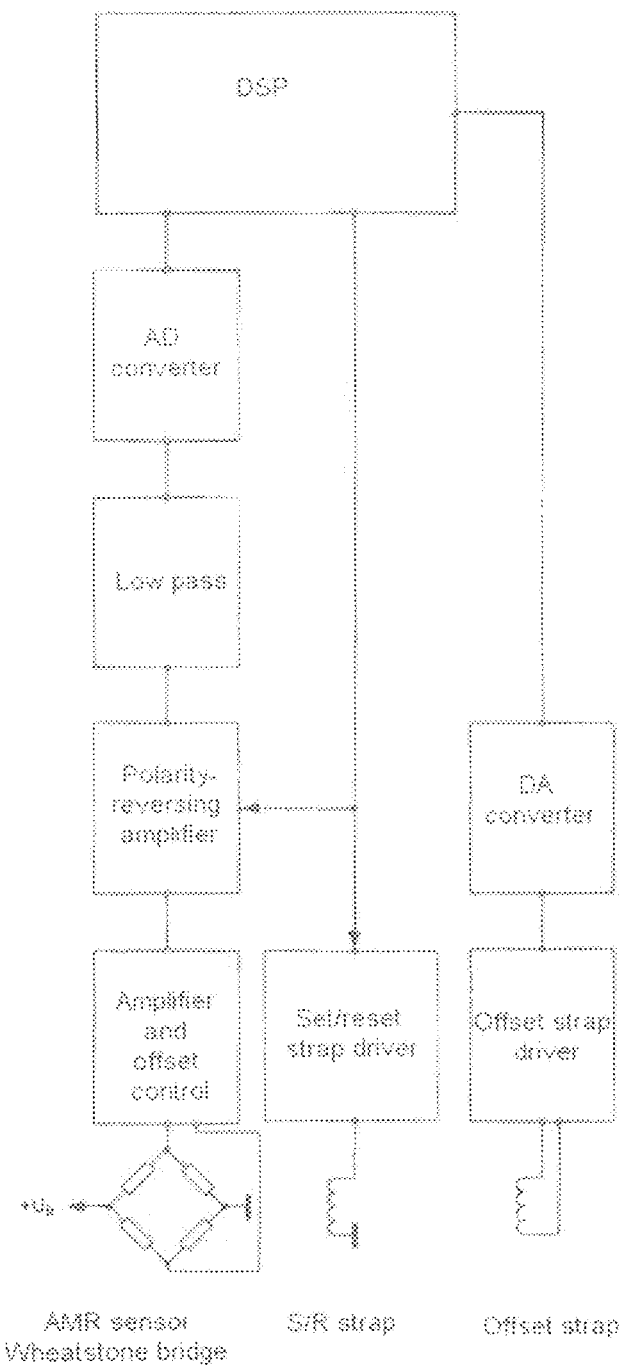

FIG. 11 shows the block circuit diagram for an AMR sensor. Via a driver, set and reset pulses were connected periodically alternately to the set-reset strap of the AMR sensor, by which means the characteristic curve of the sensor was inverted periodically. By means of this measure, an offset voltage occurring with respect to a reference voltage and independent of the magnetic flux was automatically controlled out in the following amplifier.

Via a polarity-reversing amplifier and a low pass, the actual signal modulated by the set and reset pulses was recovered. The signal was then digitized and fed to the DSP for further processing. "DSP" is the abbreviation for a digital signal processor. As opposed to the processors for PCs for digital signal processing, digital signal processors are optimized under real-time conditions. They are known to those skilled in the art and are used, for example, for speech and image processing and in instrumentation. On their chip they have, for example, a plurality of computing units, memories, various counters, peripherals for communication, universal interfaces, AD and DA converters, which can be used in parallel, and also a different command structure. In this example, a complete computer integrated into one circuit was therefore used, specifically an ADSP-BF504F from Analog Devices, which is a variant from the Blackfin family, http://www.analog.com/en/processors-dsp/blackfin/adsp-bf504f/processors/product.html.

With the aid of the offset strap, it was possible to compensate partly for the measured magnetic field. For this purpose, in the event that a threshold value was not reached or was exceeded, the current through the offset strap was adapted by increasing or reducing the output value for the DA converter. With an 8-bit DA converter, the measurement range could thus be subdivided into 256 segments. As a result, the sensor could be operated in the region of the greatest sensitivity and linearity with a simultaneously drastically minimized cross-sensitivity. In addition, the resolution was improved, since the control range of the AD converter was restricted to the magnitude of a segment plus a required overlap interval between the segments.

Since relatively high currents were required for the compensation of magnetic fields by the offset strap because of the low number of windings of the integrated coils, in this operating mode the operating time achievable with a predefined accumulator capacity would have had to be lowered. However, a remedy was created by the active measuring time of each AMR sensor being reduced and the offset strap always being moved into the neutral region via the DA converter between the measurements.

Figure 12A:
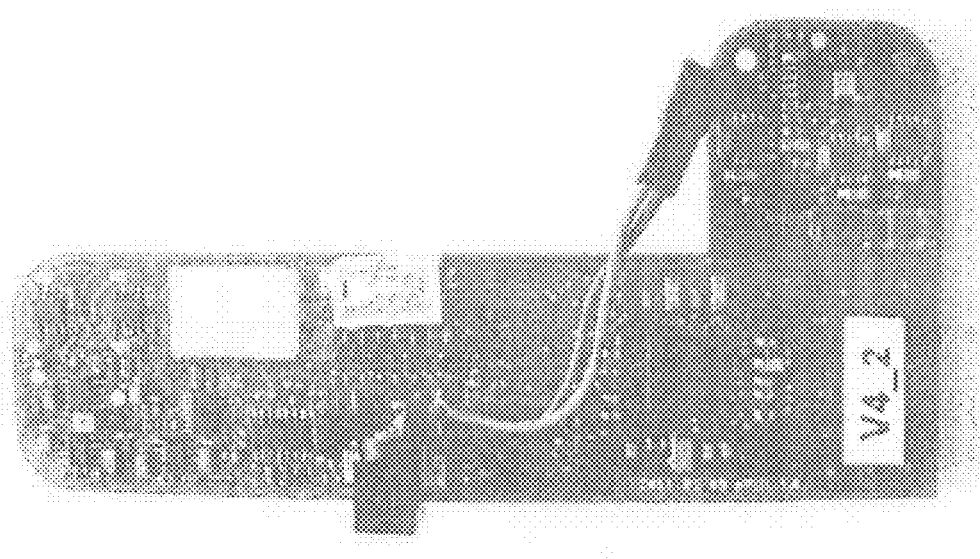
Figure 12B:
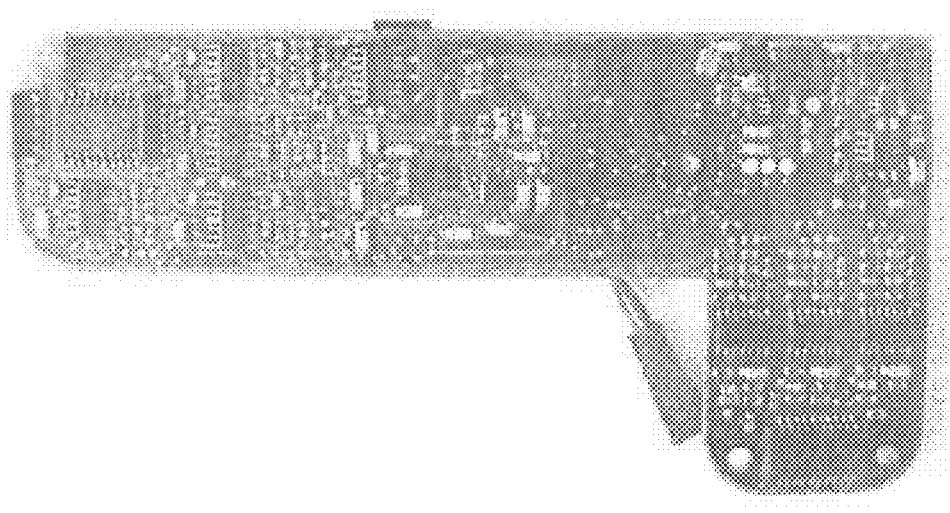

The upper side of one of the two identically constructed sensor assemblies according to the invention belonging to the detector system according to the invention is shown by FIG. 12 A, and the underside of the same by FIG. 12 B.

In general, the parameters of the AMR sensors and their components are subject to scattering. As a result, even in the case of completely identically constructed electronics, deviations which are not associated with a different direction or intensity of magnetic fields arise in the measured results. Even in the case of a simple positional change in the sensor assembly in a homogenous magnetic field, such deviations lead to erroneous changes in the calculated magnitudes of the vectors of the magnetic flux densities from the components obtained from the individual AMR sensors. In order to permit a movement of the detector arrangement in the magnetic field, even during the detection of weak measured signals, without this leading to systematic measurement errors, exact adjustment and calibration of each AMR Sensor is necessary. In the ideal case, such an adjustment would have to be carried out in a field-free room, a so-called zero chamber.

Figure 13:
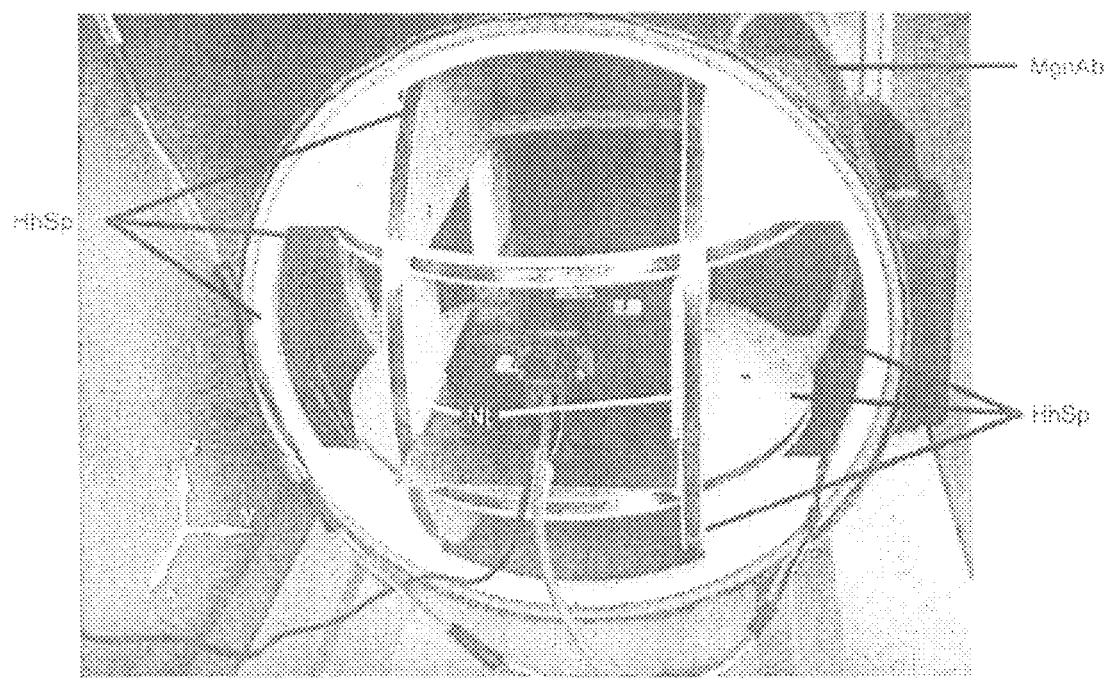

In order to produce the latter approximately, an arrangement comprising three Helmholtz coil pairs, the coil currents of which were set manually, was provided for the AMR sensors. This device was moved into a cylindrical housing, which had a magnetic shield comprising 5 layers of 0.1 mm thick Mu-metal foil. The cylindrical housing was a 600 mm long KG tube DN 300. FIG. 13 shows this arrangement comprising three Helmholtz coil pairs (HhSp) and the cylindrical part of the magnetic shield (MgnAb), which rested on a cylindrical housing. The magnetic flux density was measured in the manner known to those skilled in the art by using a Honeywell HMR 2300 magnetometer.

A shielding factor of at least 7.27 was achieved. The effects on the achievable shielding factor of the constructionally necessitated gaps at the ends of the cylindrical housing were reduced by a 40 mm wide overlap between the housing and the top shielding thereof, which is not shown in FIG. 13. The partly automated performance of the measurements required for the adjustment is known to those skilled in the art. It was achieved with the aid of drive electronics which permitted both manual zero point compensation and also the control of the coil currents through DA converters and the measurement of the currents via AD converters.

In the center of the coil arrangement, a homogenous magnetic field was generated, wherein the region in which the error was less than 0.25% depended on the coil size, specifically in the axial direction in the z range of ±2.6 cm and in the x range of ±3 cm. For a range of at least ±1.5 cm in each axial direction, deviations of less than 0.03% were achieved.

The spacing of the pairs of coils was different since, for the homogenous field distribution in the interior of each pair of Helmholtz coils, the coil spacing must be equal to the radius of the coils. Since, in the coil arrangement, the coils had to be nested inside one another, different coil diameters had to be chosen. The spacings of the coils were 135 mm, 126 mm and 115 mm respectively. The coil formers of the pairs in the y direction (tripod in FIG. 13) had grooves (Nt), into which the circuit boards having the sensor assemblies or AMR sensors fixed thereto could be pushed. Therefore, secure positioning of the circuit boards during the adjustment was provided.

Software which took account of the fact that different adjustments were expedient for the different measured objects, specifically the magnetometer with flux gate probe from Projekt Elektronik Berlin, the magnetometer with AMR sensors from Honeywell and the sensor variants with and without segmentation of the characteristic curve was created for the measurements. The software made it possible, both for a freely selectable direction x, y or z (tripod, FIG. 13), to run through a current ramp and also to record the measured values, obtained from this impressed current, of the AMR sensors positioned in the center of the coil arrangement. The axes of weak magnetization thereof were in each case positioned parallel to one of the directions x, y or z. For the current ramp, upper and lower limit and the step width could be predefined. In addition, the waiting times following specific events could be defined. These events were the reaching of the starting point of the ramp, the flip pulse to the AMR Sensor, the segment change of the sensor, change in the coil current. The characteristic curves of the coils as a function of the coil current in each case, likewise necessary for the adjustment, were determined previously, use being made of a flux gate probe of the type GeoX from Projekt Electronik, Berlin and likewise a magnetometer from Honeywell, type HMR 2300.

The functional relationship obtained in this way between the measured AMR sensor signals and the magnetic induction linked with the coil current was tabulated in the manner known to those skilled in the art for the entire control range and, respectively, for all 256 segments. From the data obtained in this way, sensitivities and cross-sensitivities were calculated and transferred to configuration files.

The adjustment of the sensor assemblies preceded all the following examples. The recording of the measured signals from the two sensor assemblies was carried out by means of the graphic programming system "LabVIEW" (National Instruments company) on a commercially available computer. The measured data was copied automatically into an Excel table, from which the data was displayed graphically.

Example 2

Two magnetite tablets were produced as in example 1 (a) but, as distinct therefrom, one of these tablets with a coating. The finished capsule is illustrated schematically in FIG. 14 A. One of the magnetite tablets (m0) was given no coating, so that upon contact with the hydrochloric acid of the simulation model, no retardation of the dissolution occurred. The other magnetite tablet (mc) received a 2 mg coating. Using the two magnetite tablets, the procedure was as in example 1 (a), and a hard gelatin capsule was then assembled in accordance with said example.

Following the use of the magnetization device, the capsule was put into the simulation model.

The simulation model (FIG. 10) was designed as in example 1 (b), and the sensor assemblies were installed at a spacing of 10 cm and an angle of 0°. The adjustment of the AMR sensors was carried out as in example 1 (c).

The measured signals were evaluated by a small characteristic curve range around the zero crossover being used with high resolution. If a predefined range was not reached or was exceeded, equivalent to an impending overload of the AD converter, the range was adapted by means of a current through the offset strap. This adaptation was carried out with the aid of an 8-bit digital-analog converter in 256 steps. During the calibration, for all the sensor channels straight-line approximations were determined for each of the 256 segments of the characteristic curve, and the corresponding slopes and zero crossovers were stored.

Figure 14:
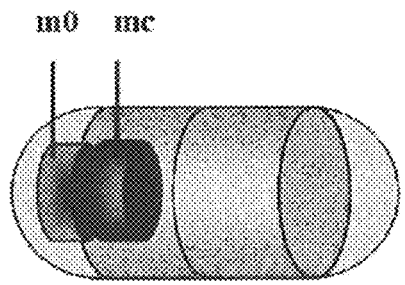
Figure 14:
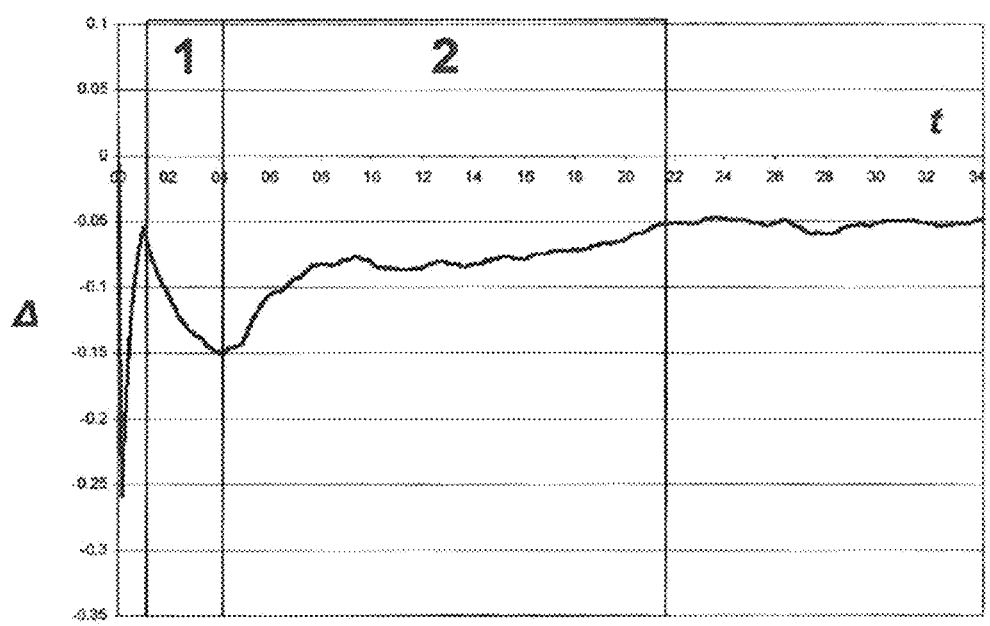

The measured signals in the x, y, z direction of the respective sensor assembly were the components of the vectors $S_1$ and $S_2$, in each case as a function of the time. FIG. 14 B shows the difference $\Delta$ in $\mu T$ in the magnitude of these vectors as a function of the time t in minutes.

At the time t=0, the capsule was kept for a few seconds in the esophagus (Sp) of the simulation model, by which means the oral ingestion was simulated. The capsule slid through the esophagus into the flask (Zh) of the simulation model. Approximately at the time t=1 min in the hydrochloric acid receiver of the flask, the first magnetite tablet disintegrated completely during the time period of about 3 min, which could be detected by $\Delta$ reaching a local minimum. The behavior of the difference $\Delta$ was determined in the interval (1) by the gradual weakening of the magnetic flux of the first magnetite tablet without coating, associated with the disintegration thereof, as compared with the second, still completely intact tablet. Starting from this minimum at the time approximately t=4 min, the system according to the invention accordingly still detected only the magnetic flux from the second magnetite tablet, which was coated with a 2 mg coating, and which disintegrated during a further 18 min, to be detected in the approach of $\Delta$ to the approximately time-constant course starting from the end of the time interval (2).

Example 3

Figure 15:
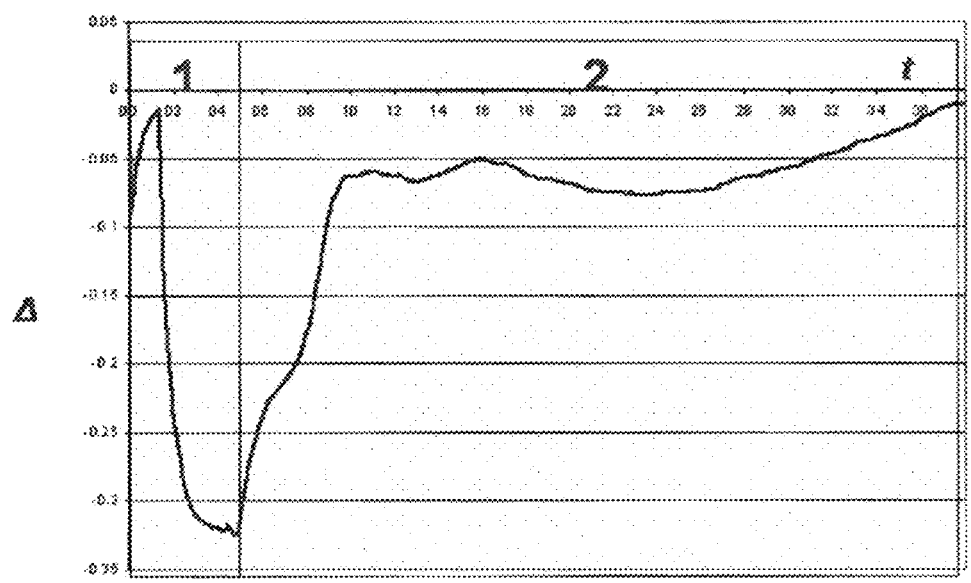

This example was carried out as in example 2 but, as distinct therefrom, with magnetite tablets which were provided with other coatings. One magnetite tablet was given a 2 mg coating, on the other hand, the other a 4 mg coating. The behavior of the difference 4 as a function of the time is illustrated in FIG. 15.

The oral ingestion, the loading of the simulation model, and the disintegration of the magnetite tablet provided with a 2 mg coating resulted in the time course in the interval (1). The disintegration of the first magnetite tablet was observed until approximately the time t=5 min. Starting from the end of the interval (1), the disintegration of the second magnetite tablet, provided with a 4 mg coating, began, which was completed approximately at the time t=37 min, at the end of the interval (2).

Example 4

Figure 16:
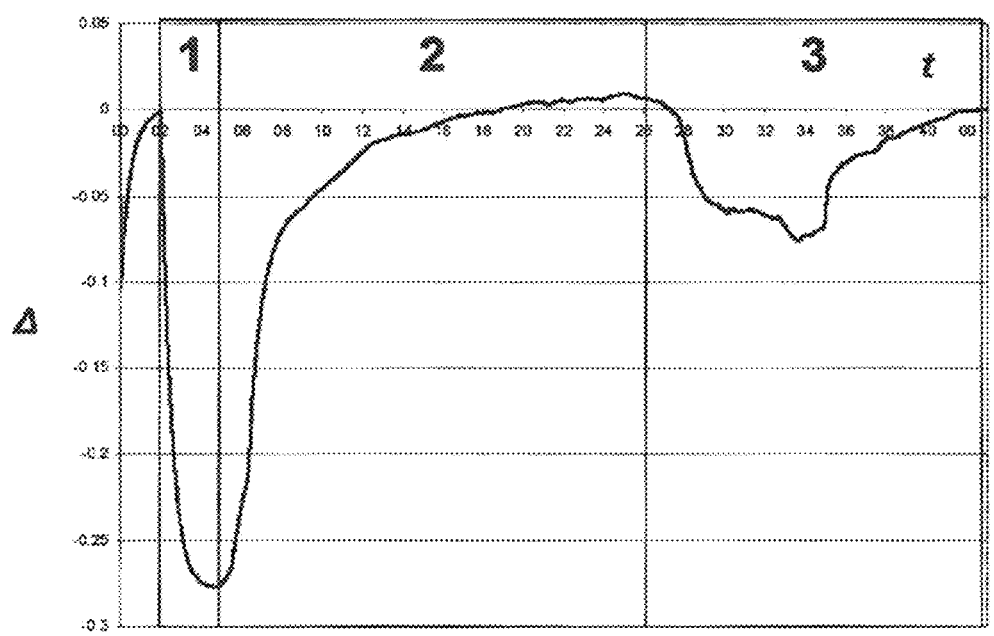

This example was carried out as in example 2 but, as distinct therefrom, with three magnetite tablets provided with different coating. The arrangement of these magnetite tablets in the capsule was as shown in FIG. 5 C. One magnetite tablet was given no coating, a second a 2 mg coating, on the other hand the third a 6 mg coating. The behavior of the difference as a function of the time is illustrated in FIG. 16.

The oral ingestion and the loading of the simulation model were completed at the time t=2 min. The disintegration of the magnetite tablet not provided with coating was observed until the time t=5 min, during the interval (1).

Thus, the magnetic fluxes of the two remaining magnetite tablets predominated, of which the one provided with a 2 mg coating disintegrated until the end of the interval (2), during the following approximately 21 min. The third magnetite tablet with a 6 mg coating was disintegrated during a further 16 min in the course of the interval (3).

Example 5

Figure 17:
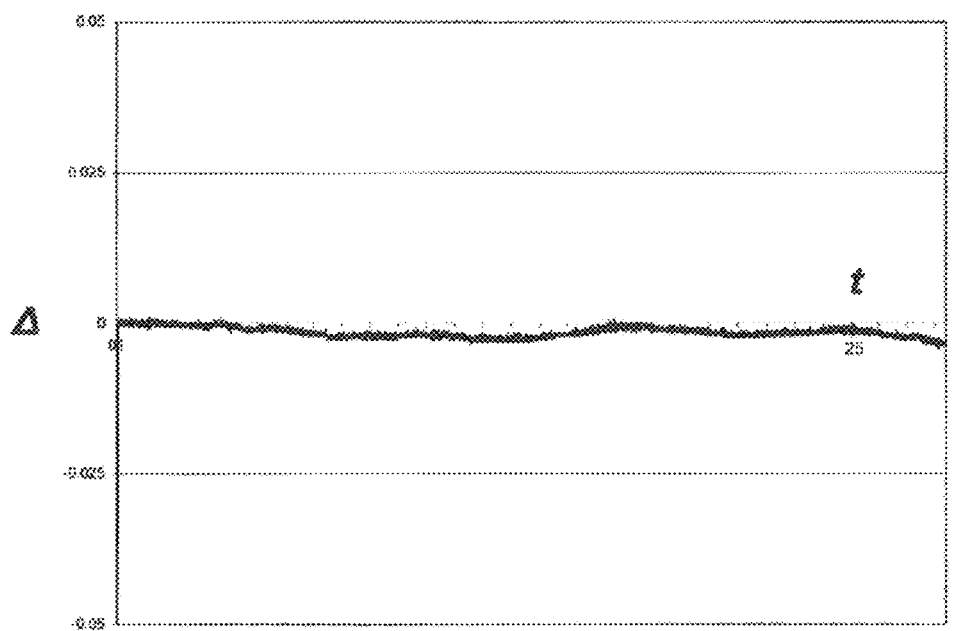

This example was carried out as in example 2 but without any magnetite tablets. The difference Δ as a function of the time during 25 min showed low fluctuations around a magnetic flux close to zero. It is supposed that the low values were to be measured on the basis of residues or traces of the surrounding interfering magnetic field being scattered in. The result, illustrated in FIG. 17, makes the absence of the magnetic body plausible.

Example 6

Figure 18:
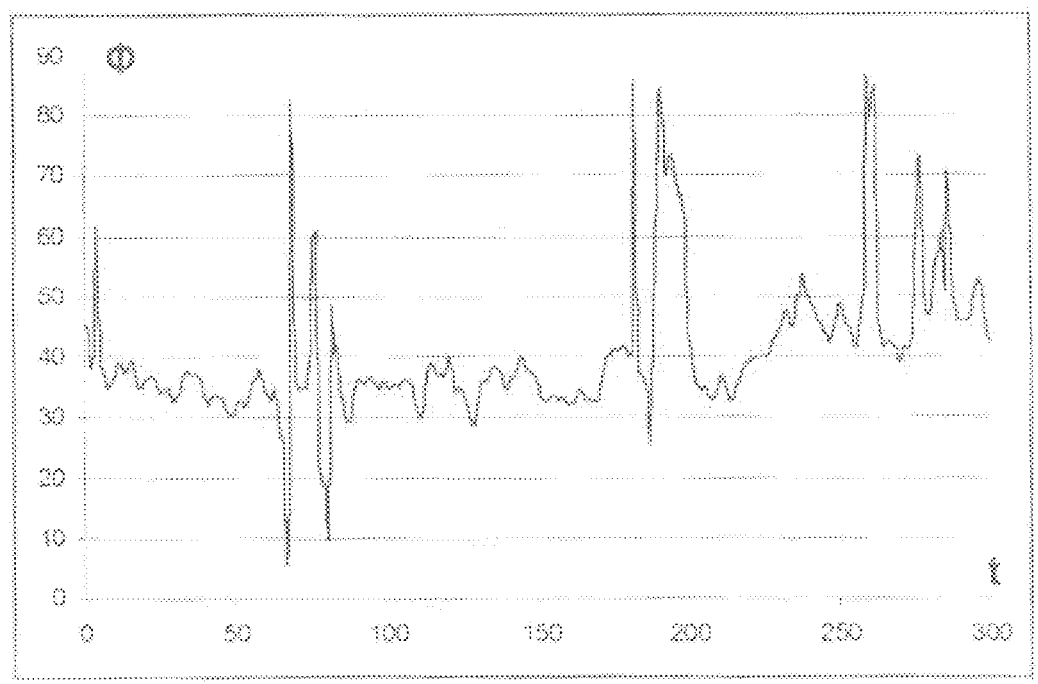

This example was carried out as in example 2 but the sensor assemblies were tilted with respect to each other at an angle of 45°, the hard gelatin capsule as the magnetic body was merely a magnetite tablet, and the flask (Zh) of the simulation model was without any hydrochloric acid receiver, so that disintegration was not possible. FIG. 18 shows the angle $\Phi$, $\Phi=\arccos(S1 \cdot S2/|S_1\|S_2|)$, plotted in degree units as a function of the time in seconds.

At the time t=0 s, the capsule was kept for some seconds in the esophagus (Sp) of the simulation model, by which means the oral ingestion was simulated. Approximately at the time t=5 s, the capsule slipped past the sensor assemblies, so that the angle $\Phi$ was changed briefly to about 60°. Between the times at about t=60 s to t=90 s, 170 s to 210 s and beginning at about 260 s, the air stream introduced into the flask (Zh) was increased in such a way that the movement of the hard gelatin capsule changed from occasional rolling and tilting to considerably more intense rotational and tumbling movements.

The invention claimed is:

1. A detector system comprising
   at least two sensor assemblies, wherein each sensor assembly has two or three anisotropic magnetic resistance (AMR) sensors, wherein the axes of weak magnetization of the sensors point in different directions in pairs, and each sensor assembly has a spacing of 0.5 to 50 cm from another sensor assembly, and
   at least two of said sensor assemblies are tilted at an angle of 0 to 45° with respect to one another,
   wherein said detector system is capable of detecting magnetic bodies in the human organism.

2. The detector system as claimed in claim 1, wherein said detector system further comprises a set reset strap, an offset strap, and wherein at least one AMR sensor has four barber pole elements, wherein said barber pole elements are connected together to form a Wheatstone bridge or a Wheatstone bridge equivalent circuit.

3. The detector system as claimed in claim 1 wherein the magnetic body is a capsule or capsule with function, wherein the function is chosen from diagnostic and/or pharmacological form, and said magnetic body is swallowed by the human organism, and said magnetic body has at least one ferromagnetic component.

4. A method for detecting the magnetic flux density produced by the magnetic body in the human organism wherein said method comprises
   (a) placing the detector system of claim 1 in proximity to the human organism,
   (b) connecting a set and reset pulse to each AMR sensor at least once,
   (c) amplifying the signals from each AMR sensor via suitable signal conditioning and via at least one low pass filter,
   (d) determining the difference between the magnitudes of the vectors of the magnetic flux densities from each sensor assembly, and/or
      determining the angle $\Phi$ between the vectors from the measured signals from the AMR sensors.

5. The method as claimed in claim 4, wherein the contribution of each AMR sensor or the measured signal obtained in (d) is filtered by a median filter.

6. The method as claimed in claim 4, wherein in (c) at least one low pass filter has a cut-off frequency selected from the group consisting of 0.1-0.99 mHz, 1 mHz-0.99 Hz, 1 Hz-9.99 Hz, and 10 Hz-1 kHz, or a combination of low pass filters having at least two different cut-off frequencies selected from said cut-off frequency group are used.

7. A method for detecting the oral administration form and for determining the time or times of the disintegration of the magnetic component in the digestive tract comprising detecting the magnetic flux density produced by the magnetic body in the human organism as in the method in claim 4.

8. The method as claimed in claim 7, wherein said measured signals are stored in a data storage device.

9. The method as claimed in claim 7 wherein said method is performed in a data management network.

10. The method as claimed in claim 7, wherein said method is performed in therapy, diagnosis and/or nutrition.

11. The method as claimed in claim 8, wherein the information on the data storage device is transmitted to a receiving device upon the receipt of a requested signal.

12. The method as claimed in claim 11 wherein said method is performed in a data management network.

13. The method as claimed in claim 11 where said method is performed in therapy, diagnosis and/or nutrition.

* * * * *